United States Patent
Gerke et al.

(10) Patent No.: US 11,291,174 B2
(45) Date of Patent: Apr. 5, 2022

(54) METHODS FOR SIMULTANEOUS POOLED GENOTYPING

(71) Applicant: PIONEER HI-BRED INTERNATIONAL, INC., Johnston, IA (US)

(72) Inventors: Justin P Gerke, Urbandale, IA (US); Heather Renee Snowgren Erickson, Ankeny, IA (US); Frank Technow, Waterloo (CA)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 17/229,818

(22) Filed: Apr. 13, 2021

(65) Prior Publication Data
US 2021/0307274 A1    Oct. 7, 2021

Related U.S. Application Data

(63) Continuation of application No. 16/096,932, filed as application No. PCT/US2017/030754 on May 3, 2017.

(60) Provisional application No. 62/335,346, filed on May 12, 2016.

(51) Int. Cl.
| | |
|---|---|
| *A01H 1/04* | (2006.01) |
| *C12Q 1/6827* | (2018.01) |
| *G16B 20/00* | (2019.01) |
| *G16B 40/00* | (2019.01) |
| *G16B 20/40* | (2019.01) |
| *C12Q 1/6895* | (2018.01) |

(52) U.S. Cl.
CPC .............. *A01H 1/04* (2013.01); *C12Q 1/6827* (2013.01); *C12Q 1/6895* (2013.01); *G16B 20/00* (2019.02); *G16B 20/40* (2019.02); *G16B 40/00* (2019.02)

(58) Field of Classification Search
None
See application file for complete search history.

(56) References Cited

U.S. PATENT DOCUMENTS

2010/0095394 A1* 4/2010 Bink ............. G16B 20/20
800/264

FOREIGN PATENT DOCUMENTS

WO      02/48387 A2   6/2002

OTHER PUBLICATIONS

Spindel et al., 2013, Bridging the genotyping gap: using genotyping by sequencing (GBS) to add high-density SNP markers and new value to traditional bi-parental mapping and breeding populations, Theor. Appl. Genet. 126: 2699-2716, with supplemental data.*
Li, 2006, Statistical Models of Sequencing Error and Algorithms of Polymorphism Detection, PhD Thesis, University Of Southern California, pp. 1-133.*
Jacobson et al., 2014, Marker Imputation Before Genomewide Selection in Biparental Maize Populations, The Plant Genome 8(2): 1-9.*
Schulz-Streeck et al., 2012, Genomic Selection using Multiple Populations, Crop Science 52: 2453-2461.*
Xu et al., 2012, Whole-genome strategies for marker-assisted plant breeding, Mol. Breeding 29: 833-854.*
Kover et al., 2009, A Multiparent Advanced Generation Inter-Cross to Fine-Map Quantitative Traits in *Arabidopsis thaliana*, PLoS Genetics 5(7), e1000551, pp. 1-15.*
Rincent et al., 2012, Maximizing the Reliability of Genomic Selection by Optimizing the Calibration Set of Reference Individuals: Comparison of Methods in Two Diverse Groups of Maize Inbreds (*Zea mays* L.), Genetics 192: 715-728.*
Technow et al., 2014, Genome Properties and Prospects of Genomic Prediction of Hybrid Performance in a Breeding Program of Maize, Genetics 197: 1343-1355.*
Bhatia, D., et al.: "Genotyping by sequencing, its implications and benefits", Crop Improvement, Jan. 1, 2013 (Jan. 1, 2013), vol. 40, No. 2, pp. 101-111.
Chi, Xiao-Fei, et al.: "An optimal DNA pooling strategy for progressive fine mapping", Genetica, May 28, 2008 (May 28, 2008), vol. 135, No. 3, pp. 267-281.
Curnow, Robert N., et al.: "Pooling DNA in the identification of paretns", Heredity, Jan. 1, 1998 (Jan. 1, 1998), vol. 80, No. 1, pp. 101-109.
Henshall, John M., et al.: "Quantitative analysis of low-density SNP data for parentage assignment and estimation of family contributions to pooled samples", Genetics Selection Evolution, Sep. 2, 2014 (Sep. 2, 2014), vol. 46, No. 1, pp. 1297-9686.
Kover, Paula X., et al.: "A Multiparent Advanced Generation Inter-Cross to Fine-Map Quantitative Traits in *Arabidopsis thaliana*", PLoS Genetics, Jul. 10, 2009 (Jul. 10, 2009), vol. 5, No. 7, p. e1000551.
Spindel, Jennifer, et al.: "Bridging the genotyping gap: using genotyping by sequencing (GBS) to add high-density SNP markers and new value to traditional bi-parental mapping and breeding populations", Theoretical and Applied Genetics, Aug. 6, 2013 (Aug. 6, 2013), vol. 126, No. 11, pp. 2699-2716.
Xu, Yunbi, et al.: "Whole-genome strategies for marker-assisted plant breeding", Molecular Breeding, Feb. 3, 2012 (Feb. 3, 2012), vol. 29, No. 4, pp. 833-854.

(Continued)

*Primary Examiner* — Bratislav Stankovic

(57) ABSTRACT

Various methods are provided for determining progeny plant genotypes from a pooled sample. The methods include genotyping marker alleles in two or more progeny plants, each resulting from a different parental cross. The methods utilize in-silico deconvolution implementing Hidden Markov Modeling to determine a probability of each possible genotype for one or more marker loci in at least one progeny plant from the genetic signal generated from the pooled samples. The present methods provide for increased efficiency in genotyping progeny plants.

15 Claims, 11 Drawing Sheets

(56) References Cited

OTHER PUBLICATIONS

Zhong, Shengqiang, et al., "Using Quantitative Trait Loci Results to Discriminate Among Crosses on the Basis of Their Progeny Mean and Variance," 2007; Genetics, 177:567-576.
International Search Report and Written Opinion for International Application No. PCT/US2017/030754, dated Aug. 1, 2017.

* cited by examiner

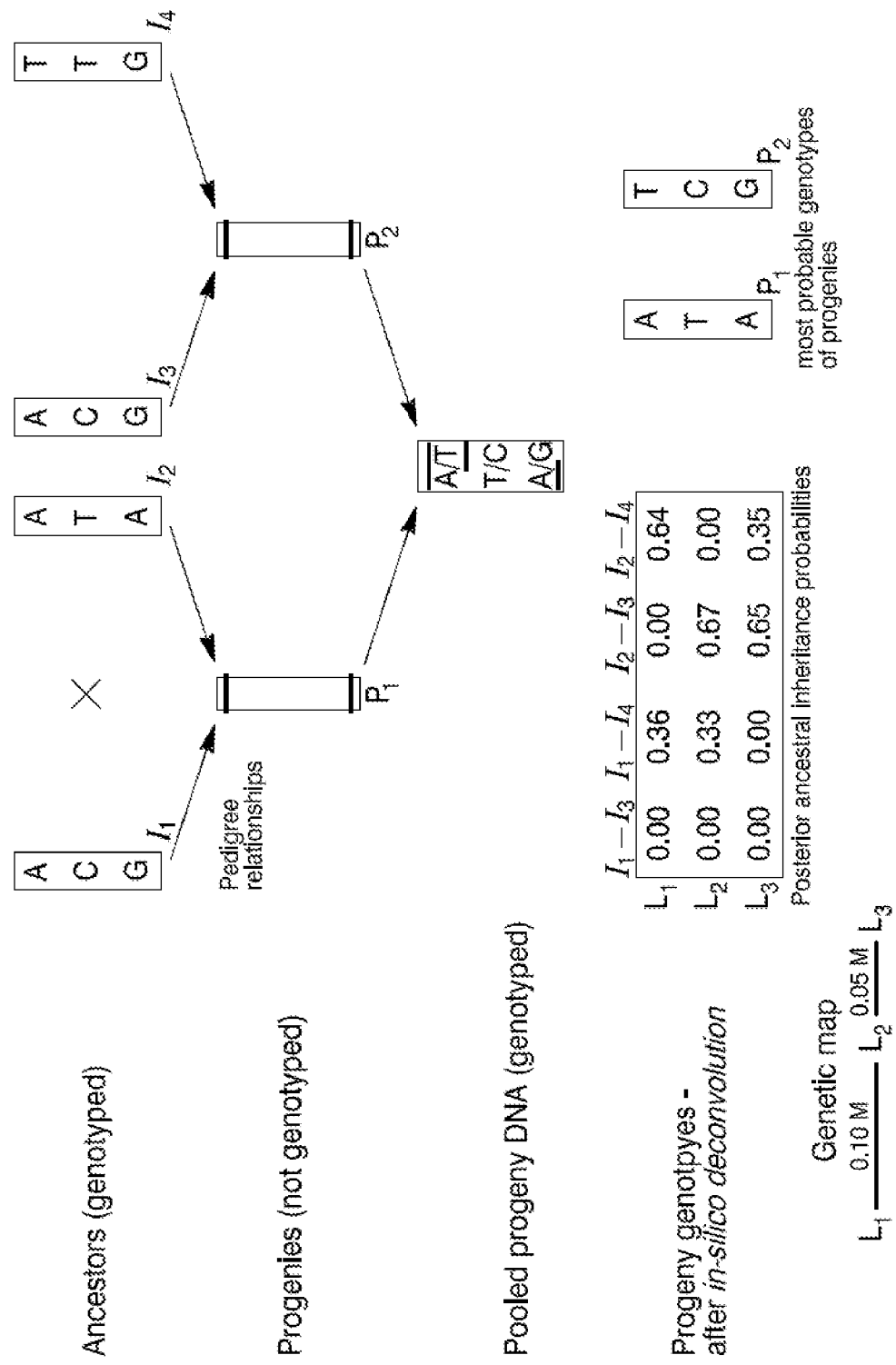

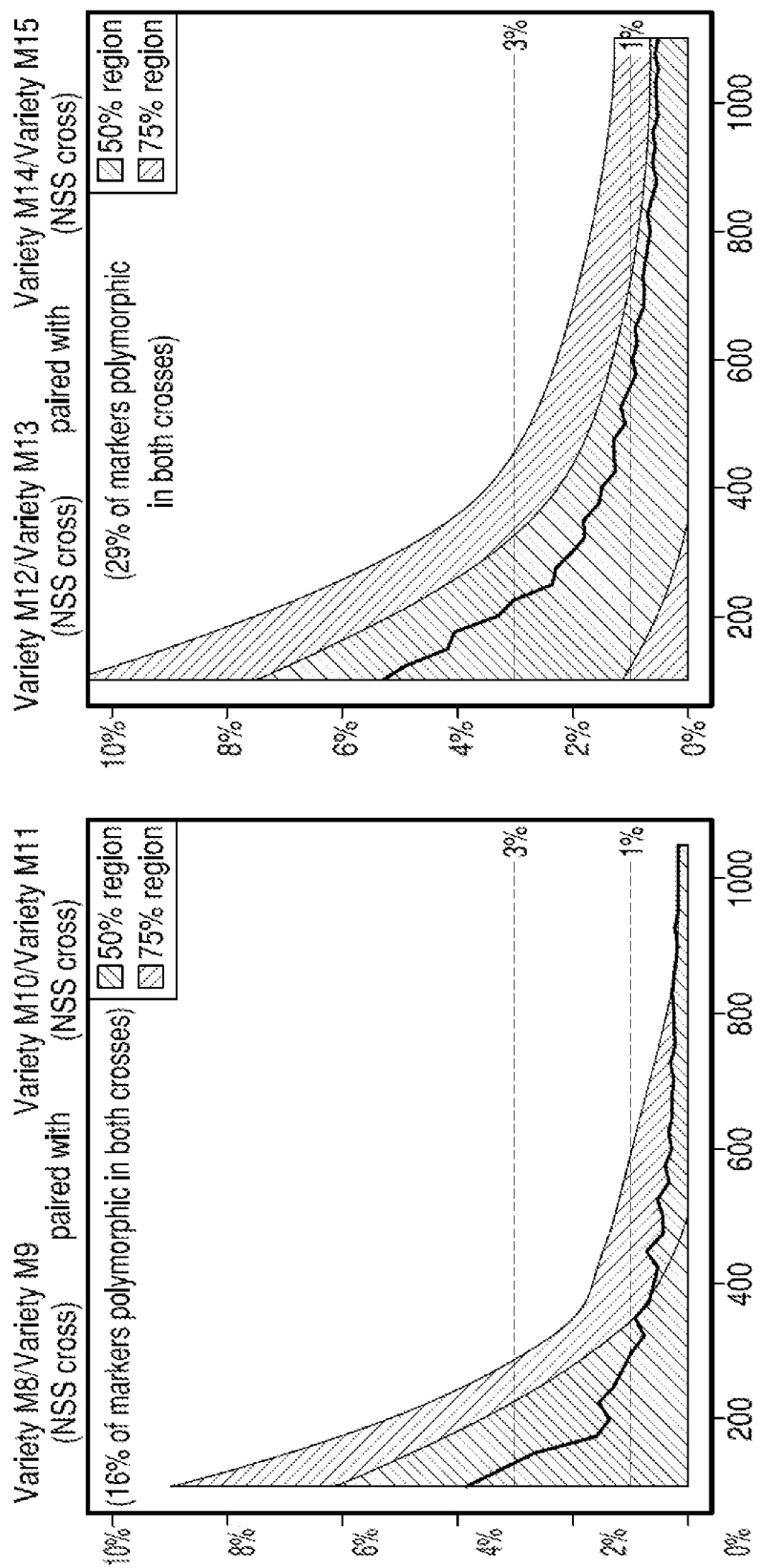

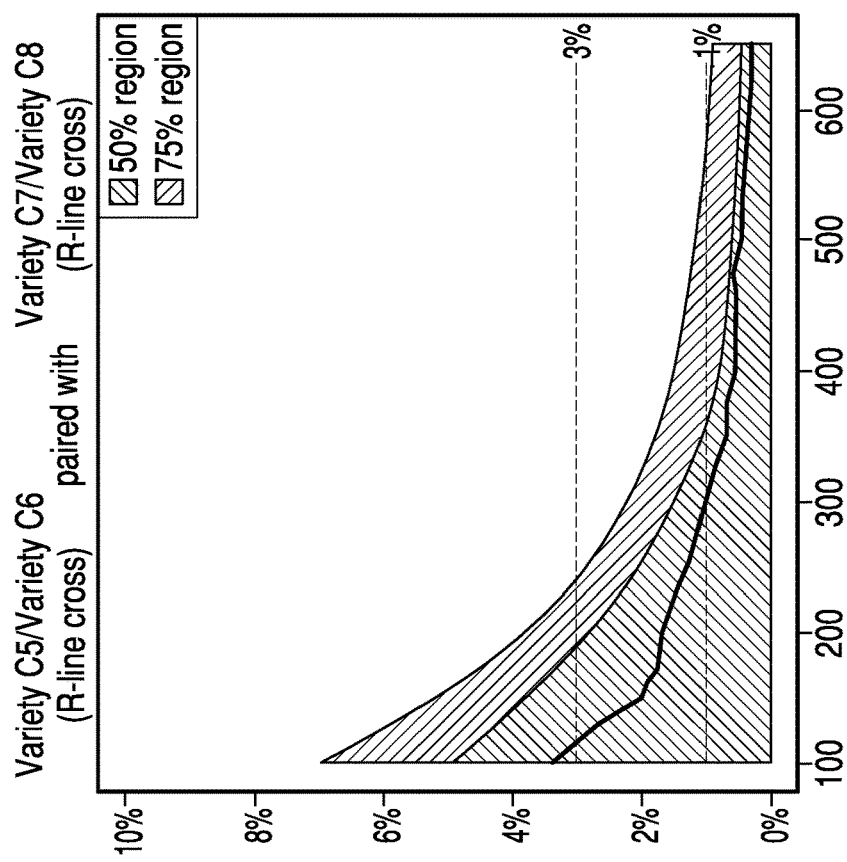
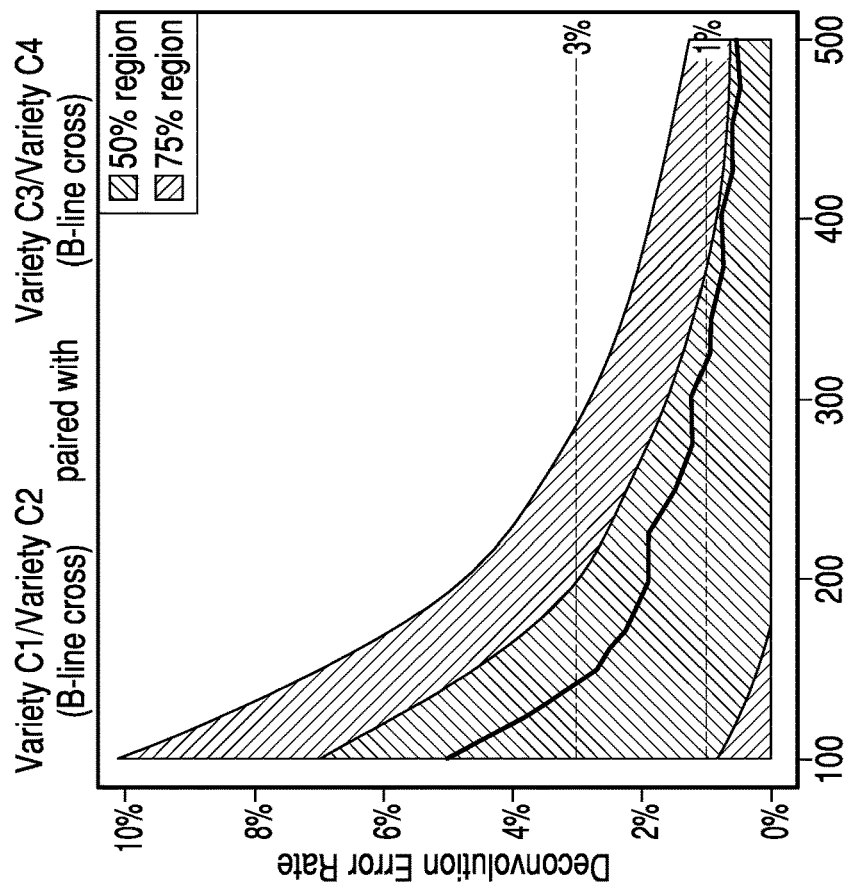

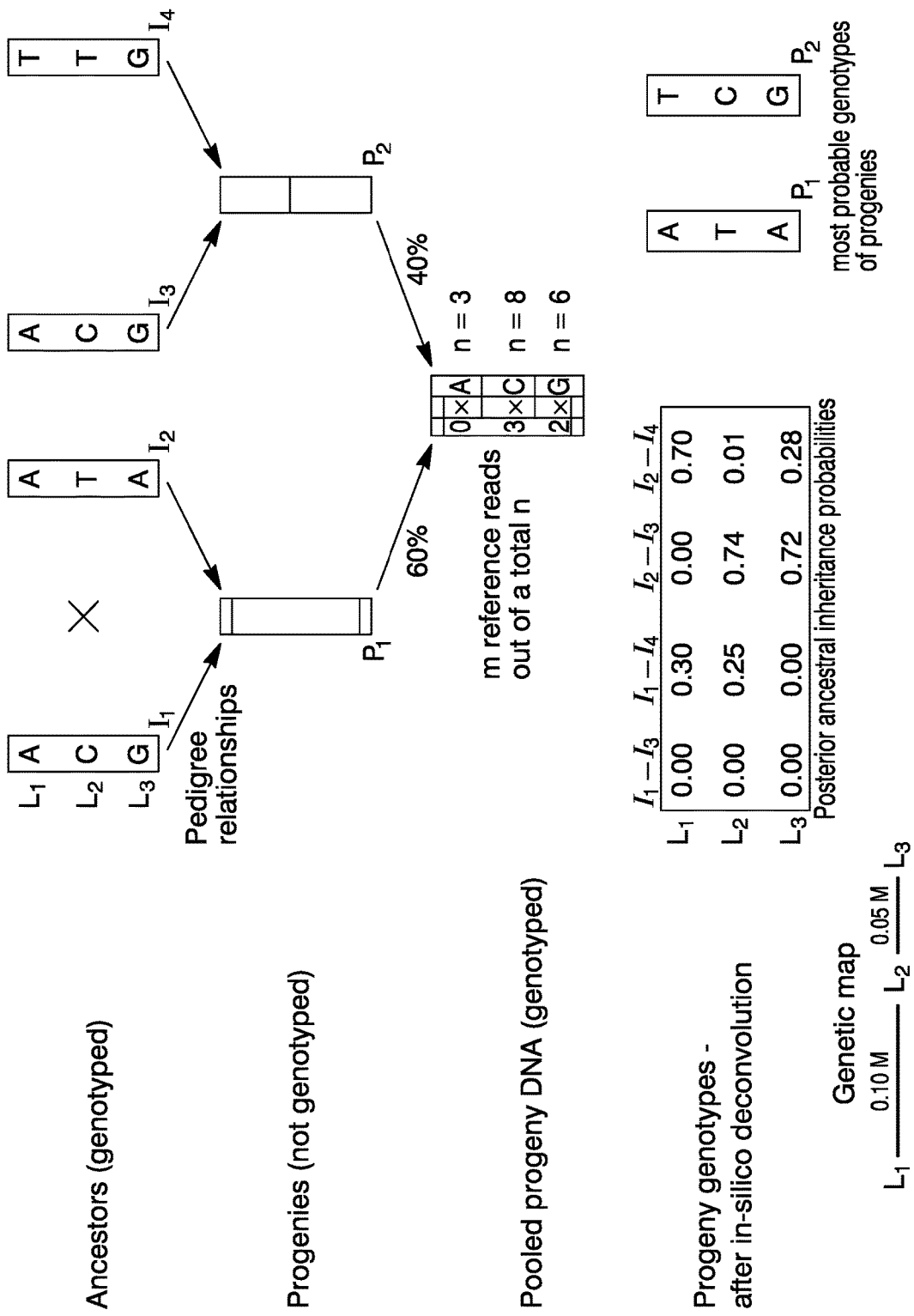

METHODS FOR SIMULTANEOUS POOLED GENOTYPING

FIELD

This disclosure relates to methods of genotyping. In particular, this disclosure relates to methods for simultaneous pooled genotyping of plant progeny resulting from crossing different pairs of parent plants.

BACKGROUND

The manipulation of crop genetics for the optimization of agronomic traits has resulted in a revolution in the seed industry. However, as many as 98% of these agronomic traits are quantitative traits, such that they are controlled by two or more genes and have measurable variability among the individual phenotypes. In order to understand and control the inheritance of these genes and the resultant phenotypes, scientists in the field have traditionally utilized methods such as quantitative trait locus (QTL) analysis.

As an outcome of QTL analysis, scientists identify chromosomal regions that are in close proximity to genes controlling a trait of interest. These chromosomal regions may be the target gene itself or may be genetic markers, such as restriction fragment length polymorphisms (RFLPs), amplified fragment length polymorphism (AFLPs), random amplified polymorphic DNAs (RAPD), variable number tandem repeats (VNTRs), microsatellite polymorphisms, single nucleotide polymorphisms (SNPs), and short tandem repeats (STRs). Because the markers are in close proximity to the genes, they tend to be inherited along with the gene (a phenomenon known as genetic linkage). As a result, the marker can be used to track the inheritance of the genes of interest. The process and statistical methods used to identify the location and effects of the various genes of interest or markers associated with these genes is referred to as QTL mapping. Recent advances in molecular genetic techniques have made available dense genetic marker maps and genotyping many individuals for these makers feasible. As such, the advent of QTL analysis thus provides a major advantage over more traditional methods for selection of agronomic traits that were based on phenotypic records of the individual plant and its ancestors.

Further, analysis of more complex populations derived from multiple founders or collected from ongoing breeding programs has the potential to significantly improve the understanding of important agronomic traits. For example, if the stability and magnitude of individual genes across different genetic backgrounds can be quantified more accurately, improved response to selection can be obtained. As an alternative to QTL mapping, whole genome regression can simultaneously estimate effects for all available markers in the genome. From these, genomic predictions of genetic value can be obtained, which then are used to inform selection decisions by a process that is called genomic selection (see, for example, Meuwissen et al., (2001) Genetics 157:1819-1829). However, breeding programs that employ genotyping of hundreds and thousands of individual genetic entities annually require large resources at high costs.

Thus, there remains a need to identify genetic markers for the detection of important agronomic traits using methods exhibiting increased efficiency in order to reduce the costs of genotyping while saving time and additional resources. The methods provided herein provide important tools for use in plant breeding programs to increase lab throughput while reducing cost.

SUMMARY

Various methods for simultaneous pooled genotyping of two or more progeny plants are provided. For instance, a method of simultaneous pooled genotyping is provided in which each progeny plant results from crossing a different pair of parent plants. In such an embodiment, the method comprising: (a) collecting: (i) genetic map distance information pertaining to one or more marker loci; (ii) genotype information for an allele of the one or more marker loci for each parent plant of a first parental cross, wherein the first parental cross produces a first progeny plant; (iii) genotypic information for an allele of the one or more marker loci for each parent plant of a second parental cross, wherein the second parental cross produces a second progeny plant; and (iv) pedigree information pertaining to the first progeny produced by the first parental cross and the second progeny produced by the second parental cross. Further, the genetic map distance information is from a plant species that is the same plant species as the parent plants. This embodiment also includes the steps of (b): providing a pooled DNA sample comprising: (i) a pooled genomic DNA sample comprising a first genomic deoxyribonucleotide (DNA) sample isolated from the first progeny plant and a second genomic DNA sample isolated from the second progeny plant; (ii) a genomic DNA sample isolated from a pooled tissue sample comprising a first tissue sample from the first progeny plant and a second tissue sample from the second progeny plant; or (iii) a genomic DNA sample isolated from an offspring produced by crossing the first progeny plant with the second progeny plant; (c) detecting in the pooled DNA sample at least one allele of each marker locus from step (a); and (d) genotyping the pooled DNA sample for at least one marker locus detected in step (c), wherein the genotyping step comprises: (i) building a first matrix for each marker locus detected in step (c) by calculating the probabilities that a pattern of inheritance at a previous marker locus can result in a pattern of inheritance at the marker locus based on the pedigree information and the genetic map distance information; (ii) building a second matrix for each marker locus detected in step (c) by calculating the probabilities that an observed genotype of the pooled genomic DNA sample could be produced by each permutation of inheritance from each parent plant in the parental cross that produced the progeny plant based on each detected allele in step (c) and the pedigree information; and (iii) determining a probability of each possible genotype for the at least one marker locus detected in step (c) in at least one progeny plant.

In some embodiments, the determining in step (d)(iii) comprises Hidden Markov Modeling comprising: (A) calculating a vector of forward probabilities at the marker locus; (B) calculating a vector of backward probabilities at the marker locus; and (C) calculating posterior ancestral inheritance probabilities at the marker locus. In other embodiments, the method further comprises calculating a vector of forward probabilities at the marker locus comprising solving for a vector of forward probabilities $f_k$ according to a following equation (I): $f_k=(T'_k f_{k-1}) \circ E_{k[m,]}$ (I); calculating a vector of backward probabilities at the marker locus comprising solving for a vector of backward probabilities $b_k$ according to a following equation (IV): $b_k=T'_k(b_{k+1} \circ E_{k[m,]})$ (IV); and calculating posterior ancestral inheritance probabilities at the marker locus comprising solving for posterior ancestral inheritance probabilities $p_k$ according to a following equation (VII): $p_k=(f_k b_{k+1}) ([f_k \circ b_{k+1}]'1)^{-1}$ (VII).

Also provided is a method for simultaneous pooled genotyping of two or more progeny plants, each resulting from crossing a different pair of parent plants, the method comprising: (a) collecting: (i) genetic map distance information pertaining to one or more marker loci; (ii) genotype information for an allele of the one or more marker loci for each parent plant from at least two different parental crosses, wherein each parental cross produces at least one progeny plant; and (iii) pedigree information pertaining to each progeny produced by each parental cross; wherein the genetic map distance information is from a plant species that is the same plant species as the parent plants. This method may further include the steps of (b) providing a pooled DNA sample comprising: (i) a pooled genomic DNA sample comprising a genomic DNA sample isolated from each progeny plant; (ii) a genomic DNA sample isolated from a pooled tissue sample comprising a tissue sample from each progeny plant; or (iii) a genomic DNA sample isolated from an offspring produced by crossing two progeny plants, each produced by a different parental cross; (c) detecting in the pooled DNA sample at least one allele of each marker locus from step (a); and (d) genotyping the pooled DNA sample for at least one marker locus detected in step (c). Further, the genotyping step may comprise: (i) building a first matrix $T'_k$ for each marker locus detected in step (c) by calculating the probabilities that a pattern of inheritance at a previous marker locus can result in a pattern of inheritance at the marker locus based on the pedigree information and the genetic map distance information; (ii) building a second matrix $E_k$ for each marker locus detected in step (c) by calculating the probabilities that an observed genotype of the pooled genomic DNA sample could be produced by each permutation of inheritance from each parent plant in the parental cross that produced the progeny plant based on each detected allele in step (c) and the pedigree information; and (iii) determining a probability of each possible genotype for at least one marker locus detected in step (c) in at least one progeny plant.

In yet other embodiments, a method for increasing genotyping efficiency of progeny plants by DNA pooling and deconvolution is provided and includes the steps of (a) collecting: (i) genetic map distance information pertaining to three or more marker loci; (ii) genotype information for an allele of the three or more marker loci for each parent plant from at least two different parental breeding crosses, wherein each parental breeding cross produces at least one progeny plant, and wherein at least one marker is polymorphic in at least one of the parental breeding crosses; and (iii) pedigree information pertaining to each progeny plant produced by each parental breeding cross; wherein the genetic map distance information is from a plant species that is the same plant species as the parent plants; (b) providing a pooled DNA sample comprising: (i) a pooled genomic DNA sample comprising a genomic DNA sample isolated from each progeny plant; (ii) a genomic DNA sample isolated from a pooled tissue sample comprising a tissue sample from each progeny plant; or (iii) a genomic DNA sample isolated from an offspring produced by crossing two progeny plants, each produced by a different parental cross; (c) detecting in the pooled DNA sample at least one allele of each marker locus from step (a); and (d) genotyping the pooled DNA sample for at least one marker locus detected in step (c), wherein the genotyping step comprises: (i) building a first matrix $T'_k$ for each marker locus detected in step (c) by calculating the probabilities that a pattern of inheritance at a previous marker locus can result in a pattern of inheritance at the marker locus based on the pedigree information and the genetic map distance information; (ii) building a second matrix $E_k$ for each marker locus detected in step (c) by calculating the probabilities that an observed genotype of the pooled genomic DNA sample could be produced by each permutation of inheritance from each parent plant in the parental cross that produced the progeny plant based on each detected allele in step (c) and the pedigree information; and (iii) determining a most probable genotype for the at least one marker locus detected in step (c) for each progeny plant.

In some embodiments, the pooled genomic DNA can include DNA from two or more different plant species.

BRIEF DESCRIPTION OF THE DRAWINGS

FIG. 2 depicts a schematic visualization of in-silico deconvolution at the three genetically linked loci $L_1$, $L_2$, and $L_3$ for a DNA pool involving two progeny plants ($P_1$ and $P_2$) from two parental breeding crosses ($I_1 \times I_2$ and $I_3 \times I_4$).

FIG. 3C depicts a graph showing the average deconvolution error rates for a simulated 2W pool in maize as a function of the number of markers genotyped. The parental cross Variety M8 x Variety M9 was paired with the parental cross Variety M10 x Variety M11. The y-axis represents the DER, and the x-axis represents the number of markers genotyped in the pool. The shaded areas indicate the 50% and 75% central probability regions.

FIG. 3D depicts a graph showing the average deconvolution error rates for a simulated 2W pool in maize as a function of the number of markers genotyped. The parental cross Variety M12 x Variety M13 was paired with the parental cross Variety M14 x Variety M15. The y-axis represents the DER, and the x-axis represents the number of markers genotyped in the pool. The shaded areas indicate the 50% and 75% central probability regions.

FIG. 4A depicts a graph showing the average deconvolution error rates for simulated canola 2W pools as a function of the number of markers genotyped. The parental cross Variety C1 x Variety C2 was paired with the parental cross Variety C3 x Variety C4. The y-axis represents the DER, and the x-axis represents the number of markers genotyped in the pool. The shaded areas indicate the 50% and 75% central probability region.

FIG. 4B depicts a graph showing the average deconvolution error rates for simulated canola 2W pools as a function of the number of markers genotyped. The parental cross Variety C5 x Variety C6 was paired with the parental cross Variety C7 x Variety C8. The y-axis represents the DER, and the x-axis represents the number of markers genotyped in the pool. The shaded areas indicate the 50% and 75% central probability region.

FIG. 7 depicts a schematic representation of a pooled genotyping assay.

DETAILED DESCRIPTION

Figure 1:
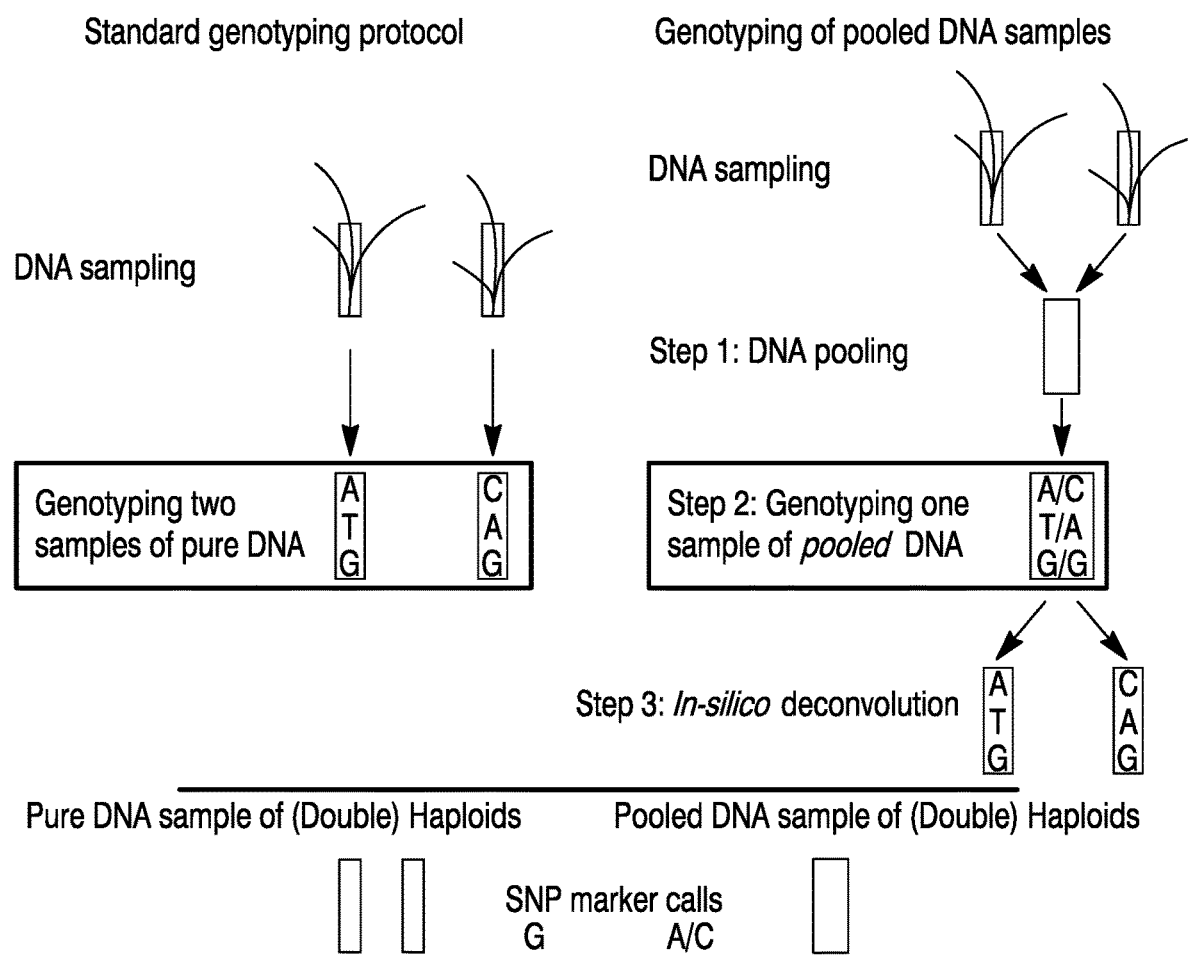
FIG. 1 depicts a schematic of a standard genotyping protocol (left) as compared to an exemplary pooled genotyping method of the present disclosure (right).
Figure 3A:
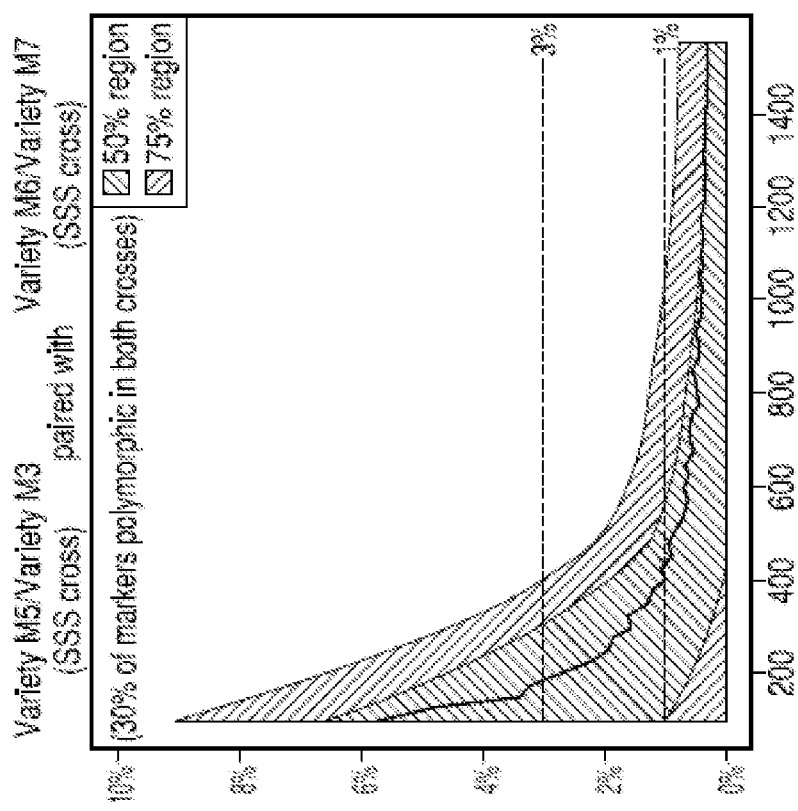
FIG. 3A depicts a graph showing the average deconvolution error rates for a simulated 2W pool in maize as a function of the number of markers genotyped. The parental cross Variety M1 x Variety M2 was paired with the parental cross Variety M3 x Variety M4. The y-axis represents the deconvolution error rate (DER), and the x-axis represents the number of markers genotyped in the pool. The shaded areas indicate the 50% and 75% central probability regions.
Figure 3B:
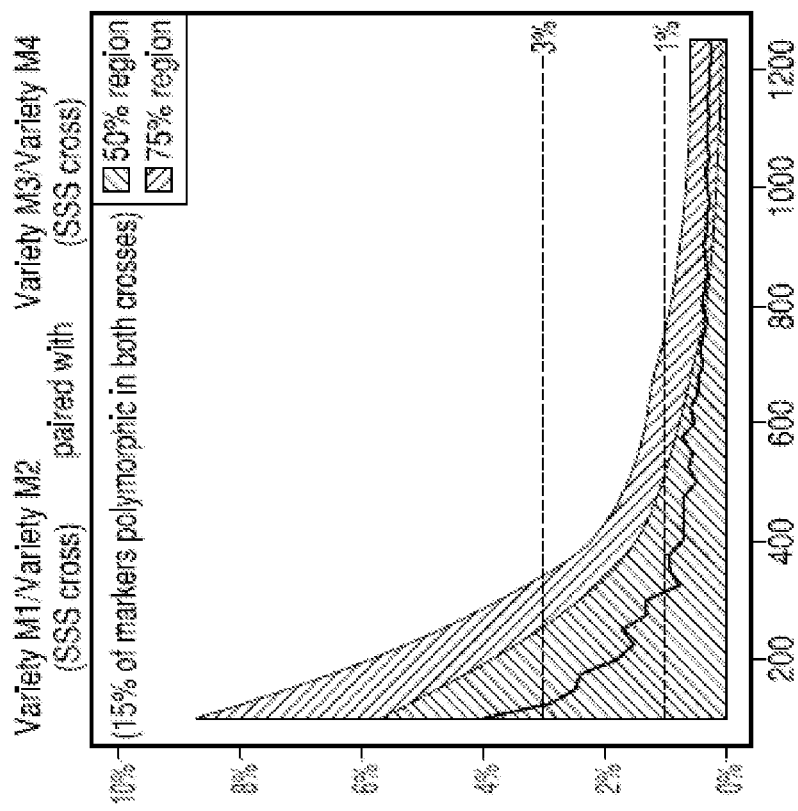
FIG. 3B depicts a graph showing the average deconvolution error rates for a simulated 2W pool in maize as a function of the number of markers genotyped. The parental cross Variety M5 x Variety M3 was paired with the parental cross Variety M6 x Variety M7. The y-axis represents the DER, and the x-axis represents the number of markers genotyped in the pool. The shaded areas indicate the 50% and 75% central probability regions.
Figure 3E:
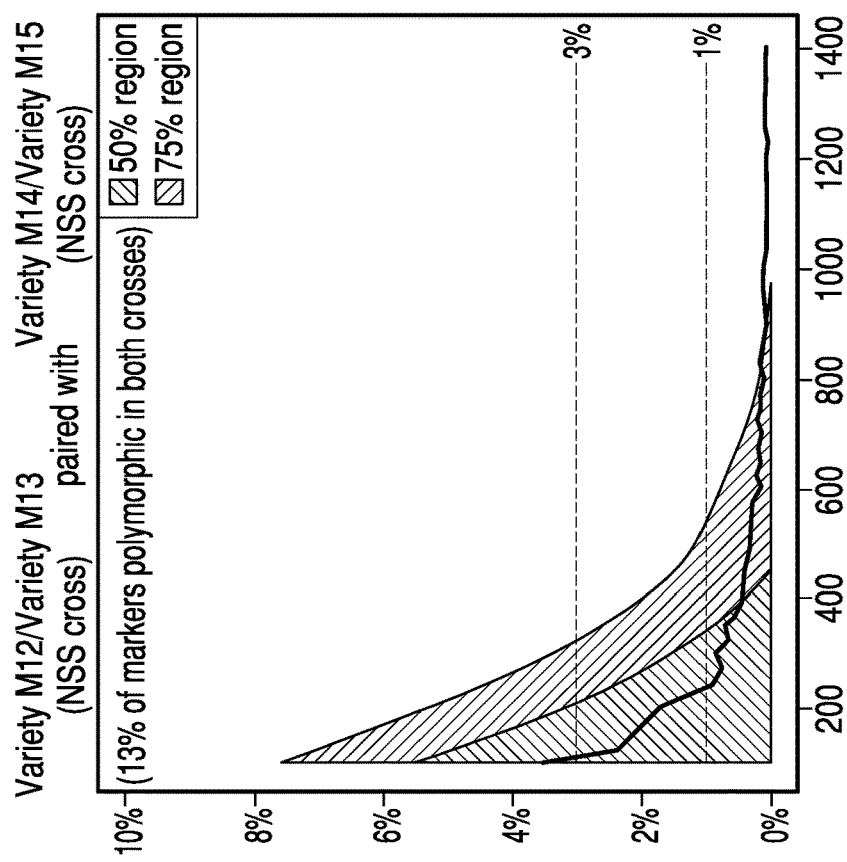
FIG. 3E depicts a graph showing the average deconvolution error rates for a simulated 2W pool in maize as a function of the number of markers genotyped. The parental cross Variety M16 x Variety M17 was paired with the parental cross Variety M18 x Variety M19. The y-axis represents the DER, and the x-axis represents the number of markers genotyped in the pool. The shaded areas indicate the 50% and 75% central probability regions. The 50% central probability regions is not visible because the 50% central probability region is effectively zero.
Figure 3F:
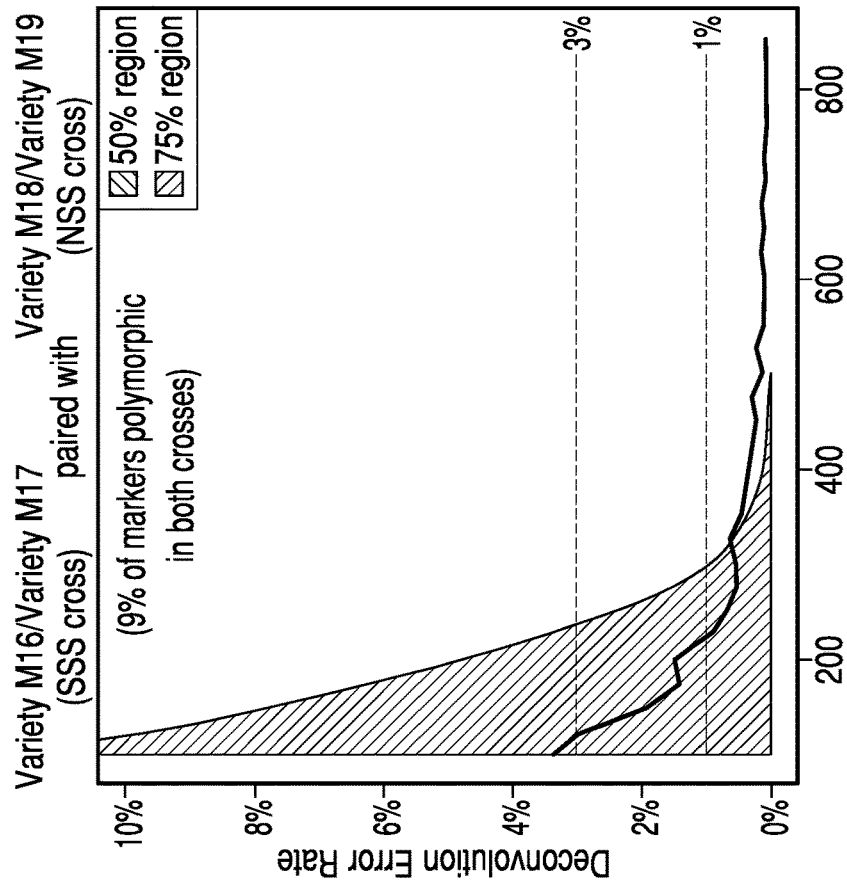
FIG. 3F depicts a graph showing the average deconvolution error rates for a simulated 2W pool in maize as a function of the number of markers genotyped. The parental cross Variety M1 x Variety M20 was paired with the parental cross Variety M14 x Variety M21. The y-axis represents the DER, and the x-axis represents the number of markers genotyped in the pool. The shaded areas indicate the 50% and 75% central probability region.
Figure 4C:
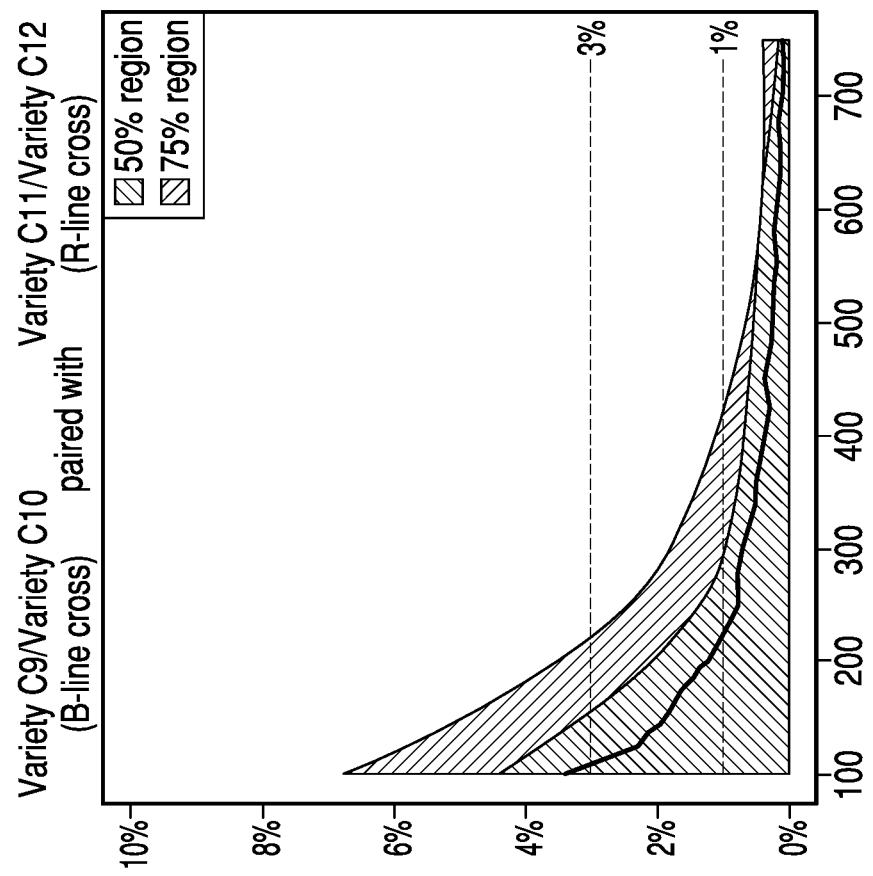
FIG. 4C depicts a graph showing the average deconvolution error rates for simulated canola 2W pools as a function of the number of markers genotyped. The parental cross Variety C9 x Variety C10 was paired with the parental cross Variety C11 x Variety C12. The y-axis represents the DER, and the x-axis represents the number of markers genotyped in the pool. The shaded areas indicate the 50% and 75% central probability region.

Provided herein methods for genotyping individuals. In a particular aspect, provided are methods for simultaneous pooled genotyping two or more progeny plants, each of which results from crossing different pairs of parent plants. In some embodiments, genomic DNA isolated from a progeny plant produced from each parent plant breeding cross is pooled to provide a pooled DNA sample. Alternatively, plant tissue from each progeny plant can be pooled, and genomic DNA can then be isolated from the pooled tissue. In still other embodiments, a progeny plant produce by a parental breeding cross is crossed with a progeny produced by a different parental breeding cross, and genomic DNA is isolated from the resulting offspring. The present methods also include a step of detecting in the pooled DNA sample (e.g., pooled genomic DNA samples, genomic DNA isolated from the pooled tissue, or genomic DNA isolated from the offspring of a progeny cross) at least one allele of one or more marker loci and then genotyping the pooled DNA sample for the marker locus. The genetic signal is then processed by in-silico deconvolution to determine a probability of each possible genotype at the marker loci in one or more of the progeny plants. In yet other embodiments, the deconvolution step implements Hidden Markov Modeling as describe elsewhere herein. The present methods utilize one or more of the following data: (1) the genotype data (i.e., the marker alleles detected) of the pooled DNA; (2) the marker genotypes of the ancestral plants (e.g., the parent plants); (3) the pedigree relationship between the pooled progeny plants and the ancestors (e.g., the parent plants); and (4) the genetic map of the genome.

It is to be understood that this disclosure is not limited to particular embodiments, which can, of course, vary. It is also to be understood that the terminology used herein is for the purpose of describing particular embodiments only, and is not intended to be limiting.

In this disclosure, a number of terms and abbreviations are used. Certain definitions used in this disclosure and claims are provided below. In order to provide a clear and consistent understanding of the disclosure and claims, including the scope to be given such terms, the following definitions apply unless specifically stated otherwise.

In addition, the disclosure of each reference set forth herein is hereby incorporated by reference in its entirety.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a pooled DNA sample comprising two genomic DNA samples may have three or more genomic DNA samples. Additionally, the term "comprising" is intended to include embodiments encompassed by the terms "consisting essentially of" and "consisting of." Similarly, the term "consisting essentially of" is intended to include embodiments encompassed by the term "consisting of."

"Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, insect resistance or tolerance, herbicide resistance, branching, flowering, seed set, seed size, seed density, standability, threshability, and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant. An allele is "favorable" for a certain phenotypic trait if that allele positively correlates with that phenotypic trait. An allele is "unfavorable" for a certain phenotypic trait if that allele negatively correlates with that phenotypic trait.

The term "amplifying" in the context of nucleic acid amplification is any process whereby an additional copy or copies of a selected nucleic acid (or a transcribed form thereof) are produced. An "amplicon" is an amplified nucleic acid, e.g., a nucleic acid that is produced by amplifying a template nucleic acid by any available amplification.

The term "associated" or "association" when used in reference to a marker, marker allele, and/or polymorphism and a phenotypic trait and/or haplotype refers to any statistically significant correlation between the presence of a given allele of a marker locus and the phenotypic trait and/or haplotype, which may be qualitative or quantitative.

"Backcrossing" is a process in which a breeder crosses a progeny variety back to one of the parental genotypes one or more times.

A "doubled haploid" as used herein refers to a plant having a genotype formed when haploid cells undergo chromosomal doubling to achieve homozygosity.

An "elite line" is an agronomically superior line that has resulted from many cycles of breeding and selection for superior agronomic performance. Numerous elite lines are available and known to those of skill in the art of plant breeding.

An "elite population" is an assortment of elite individuals or lines that can be used to represent the state of the art in terms of agronomically superior genotypes of a given crop species, such as maize.

A "recurrent" plant or "recurrent parent" plant refers to a plant typically having a genetic background with favorable agronomic traits that is crossed with a plant comprising a desired trait or allele, which is sometimes referred to as a "donor" plant or "donor parent" plant. Backcrossing then enables the breeder to transfer the desired trait or allele from the donor plant into the favored genetic background of the recurrent plant.

A "genetic map" is a description of genetic association or linkage relationships among loci on one or more chromosomes (or linkage groups) within a given species, generally depicted in a diagrammatic or tabular form.

"Genomic selection" refers to selecting individuals according to predictions of their genetic value for a set of traits obtained from estimated effects of markers that cover the entire genome. If this is applied to haploid individuals, the process is called "gamete selection."

"Genotype" is a description of the allelic state at one or more loci.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

"Heterotic" refers to a hybrid progeny plant with improved or increased function of any biological or agronomic trait as a result of mixing the genetic contributions from the parent plants.

"Heterosis" refers to a hybrid progeny plant manifesting improved or increased function of any biological or agronomic trait as a result of mixing the genetic contributions from the parent plants. "Heterotic" groups are sets of populations of plants whose hybrid progeny display heterosis when a plant from one population is crossed with a plant from a second population.

An individual is "homozygous" if the individual has only one type of allele at a given locus (e.g., a doubled haploid individual has a copy of the same allele at a locus for each of two homologous chromosomes). An individual is "heterozygous" if more than one allele type is present at a given locus (e.g., a diploid individual with one copy each of two different alleles).

"In-silico" refers to a process that is performed by computation, for example, on a computer or via computer simulation.

The terms "label" or "detectable label" refer to a molecule capable of detection. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a genetic map distance of 1.0 centiMorgan (1.0 cM) or 0.01 Morgans (M).

The genetic elements or genes located on a single chromosome segment are physically linked. In some embodiments, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosomal segment are also "genetically linked", typically within a genetic recombination distance of less than or equal to 50 cM, e.g., about 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.75, 0.5, 0.25 cM or less. That is, two genetic elements within a single chromosomal segment undergo recombination during meiosis with each other at a frequency of less than or equal to about 50%, e.g., about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.75%, 0.5%, 0.25% or less. "Closely linked" markers display a cross over frequency with a given marker of about 10% or less, e.g., 9%, 8%, 7%, 6%, 5%, 4%, 3%, 2%, 1%, 0.75%, 0.5%, 0.25% or less (the given marker locus is within about 10 cM of a closely linked marker locus, e.g., 9, 8, 7, 6, 5, 4, 3, 2, 1, 0.75, 0.5, 0.25 cM or less of a closely linked marker locus). Put another way, closely linked marker loci co-segregate at least about 90% the time, e.g., 91%, 92%, 93%, 94%, 95%, 96%, 97%, 98%, 99%, 99.5%, 99.75%, or more of the time.

"Linkage disequilibrium" is a non-random association of alleles at two or more loci wherein the two or more alleles occur together at a greater frequency than expected from their individual frequencies. "Linkage disequilibrium" can also occur between unlinked markers. It is based on allele frequencies within a population and is influenced by but not dependent on linkage.

"Locus" is a defined segment of DNA.

A "map location" or "map position" is an assigned location on a genetic map relative to linked genetic markers where a specified marker can be found within a given species. Map positions are generally provided in Morgans (M) or centiMorgans (cM).

"Mapping" is the process of defining the association and relationships of loci through the use of genetic markers, populations segregating for the markers, and/or standard genetic principles of recombination frequency.

"Marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest.

"Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Cultivar" and "variety" are used synonymously and mean a group of plants within a species (e.g., *Zea mays*) that share certain genetic traits that separate them from other possible varieties within that species. Maize cultivars may be inbred lines produced after several generations of self-pollinations (e.g., filial selfings) or may be artificially created doubled haploids. Individuals within a maize cultivar are homogeneous, nearly genetically identical, with most loci in the homozygous state.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid," "nucleic acid molecule," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Self-crossing" or "self-pollination" or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on a genome.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media or other chemical components. Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989, the content of which is incorporated herein by reference in its entirety.

Generation of Inputs for use in Deconvolution of Pooled Genotyping Data

Provided herein are methods for genotyping two or more progeny plants that are produced by different parent plant crosses. In a particular aspect, one or more marker alleles are detected in a pooled DNA sample. In some embodiments, different parental plant crosses are utilized in which each parental plant cross produces at least one progeny plant. Genomic DNA can then be extracted and purified from the progeny plant from each parental cross using any suitable genomic DNA isolation technique known in the art, such as a modified CTAB (cetyltriethylammonium bromide, Sigma H5882) method described by Stacey & Isaac (Methods in Molecular Biology, Vol. 28: Protocols for Nucleic Acid Analysis by Nonradioactive Probes, Ed: Isaac, Humana Press Inc., Totowa, N.J. 1994, Ch. 2, pp. 9-15), the content of which is incorporated herein by reference in its entirety, and pooled to produce the pooled DNA sample. In other embodiments, a pooled DNA sample comprises plant tissue (e.g., leaf punch) harvested from each progeny plant to produce a pool of progeny plant tissue from which a genomic DNA sample is isolated. In yet other embodiments, a pooled DNA sample may comprise isolating genomic DNA from an offspring that is produced from crossing a progeny from a parental cross with another progeny from a different parental cross. In some embodiments, the present methods include a step of extracting genomic DNA from progeny plants, e.g., extracting a genomic DNA sample from each of the progeny plants, extracting a genomic DNA sample from plant tissue pooled from each of the progeny plants, or extracting a genomic DNA sample from an offspring of a breeding cross between two progeny. In other embodiments, the present methods comprise obtaining progeny plant genomic DNA from, e.g., stored genomic DNA samples.

In some aspects, the present methods comprise two or more parental crosses. In other aspects, the present methods comprise three or more parental crosses. In yet other aspects, the present methods comprise four or more parental crosses, e.g., 4, 5, 6, 7, 8, 9, 10, or more parental crosses. Any number of parental crosses are suitable for use with the present methods. For instance, in some embodiments, the present methods comprise two different breeding crosses in which one parent plant has a different genotype as compared to the other three parent plants. In other embodiments, the present methods comprise two different breeding crosses in which all four parent plants have different genotypes. In still other embodiments, the present methods comprise three different breeding crosses in which one parent plant has a different genotype as compared to the other five parent plants. Alternatively, three different parental crosses are utilized in which two or more parent plants have different genotypes as compared to the remaining parent plants or where all six parent plants have different genotypes. In still other aspects, four or more different parental crosses are utilized in which two or more parent plants have different genotypes as compared to the remaining parent plants or where all parent plants have different genotypes. The type of parental crosses used with the methods provided herein can be any type of plant cross used in plant breeding programs, e.g., an $F_1$ cross, an $F_2$ cross, an $F_3$ cross, a backcross followed by filial selfing of the progeny plant, a three-way cross followed by filial selfing of the progeny plant, a four-way cross followed by filial selfing of the progeny plant, or a combination thereof. Further, the ploidy of the progeny plants produced by the parental crosses can be diploid or haploid. Preferably, the progeny plants of the present methods are haploid, double haploids, or a progeny plant derived through less than one or one or more filial selfings.

In certain aspects of the present disclosure, the parent crosses and the progeny produced are of a plant species. Plant species suitable for use with the present methods, include, but are not limited to monocots and dicots. Exemplary plant species of interest include, but are not limited to, maize (*Zea mays*), *Brassica* sp. (e.g., *B. napus, B. rapa, B. juncea*), alfalfa (*Medicago sativa*), barley (*Hordeum vulgare*), rye (*Secale cereale*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), tomato (*Solanum lycopersicum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos mucifera*), pineapple (*Ananas comosus*), citrus trees (*Citrus* spp.), peach (*Prunus persica*), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, vegetables, ornamentals, grasses and conifers. In a preferred embodiment, the plant species is selected from the group consisting of maize, wheat, rice, millet, barley, sorghum, rye, soybean, alfalfa, canola, cotton, sunflower, potato, and tomato.

In particular aspects, the present methods comprise genotyping at least one allele of one or more marker loci. In one embodiment, at least one parent plant from each of the parental crosses are genotyped for at least one allele of one or more marker locus. In other aspects, each parent plant from each of the parental crosses are genotyped for at least one allele of one or more marker locus. In some aspects, at least one progeny produced by each of the parental crosses are genotyped for at least one allele of one or more marker locus. In still other embodiments, at least one progeny produced by each of the parental crosses and at least one parent plant from each of the parental crosses are genotyped for at least one allele of one or more marker locus. In some aspects, the genotyping step comprises genotyping at least one allele of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more marker loci. In other aspects, the methods comprise genotyping at least one allele of 100, 200, 300, 400, 500, 600, 700, 800, 900, 1,000, or more marker loci. In yet other aspects, the methods comprise genotyping at least one allele of 1,000, 2,000, 3,000, 4,000, 5,000, 6,000, 7,000, 8,000, 9,000, 10,000, or more marker loci. In still other embodiments, the methods comprise genotyping at least one allele of 10,000, 20,000, 30,000, 40,000, 50,000, 60,000, 70,000, 80,000, 90,000, 100,000, 1,000,000, 10,000,000, 100,000,000 or more marker loci. It will be appreciated by the skilled artisan that genotyping may be performed by any suitable technique and may comprise detecting the at least one allele of the one or more marker locus. Suitable detection techniques are described elsewhere herein.

In some embodiments, the at least one marker locus is polymorphic in at least one parental cross used in the present methods. In other embodiments, the at least one marker locus is polymorphic in all parental crosses used in the present methods.

Also provided herein are methods of simultaneous pooled genotyping that comprises a deconvolution algorithm that includes as input one or more of the following: (1) genotype data of the pooled DNA sample obtained from the progeny plants or tissues thereof; (2) the genotypes of at least one allele from one or more marker loci from the ancestors (e.g., parent plants) that produced the progeny plants; (3) a pedigree relationship between the pooled progeny plants and their corresponding ancestors; and (4) the genetic map of the genome from a plant species that is the same plant species as the progeny plants and parent plants. As discussed above, genotype data of the pooled DNA sample and/or the parent plants may be obtained by detecting in the plant at least one allele of one or more marker loci using any suitable detection technique. In some embodiments, the present methods include one or more DNA extraction steps wherein genomic DNA is extracted from one or more parent plants and/or one or more progeny or the tissue thereof. In other embodiments, genotype information for an allele of one or more marker locus for each parent plant may be collected from, e.g., archived genotype data, it being understood that each marker allele of interest may be known in one or more parent plants. In such embodiments, it will not be necessary to extract genomic DNA from a parent plant for which the relevant genotypes are known or to detect in that parent plant the marker allele. In some embodiments, the relevant genotypes from each parent from each parental cross used in the present methods are known. For instance, some parental crosses may be between one or two parent plants commonly used in commercial breeding programs, e.g., one or more elite plant varieties. In other embodiments, the genotype information for one or more parent plants is not known. In such embodiments, genotype information pertaining to one or more marker loci from a parent plant may be obtained using genomic DNA extraction and/or detection of the one or more marker allele as described herein.

In some embodiments, pedigree information pertaining to each progeny plant produced by each parental cross is collected. For instance, a progeny produced by a parental cross may be designated or tracked such that one or both parent plants that produced the progeny plant are known (see, for example, FIG. 2). Further still, pedigree information may include grandparent plants and other ancestral lineages. Other pedigree information may include the type of cross that produced the progeny plant, e.g., $F_1$ cross, backcross, three-way cross, or four-way cross. It should be understood that collecting the pedigree information refers to any suitable process of tracking the progeny plants produced by each parental cross.

In some embodiments, the methods provided herein include the step of collecting genetic map distance information. In a preferred embodiment, genetic map distance information is collected for each marker allele being genotyped. Genetic map distance information refers to the genetic map of the plant species being genotyped. Genetic map distance information includes estimated genetic distances between the marker loci of interest (measured in Morgans (M) or centiMorgans (cMs)) and the general order of marker loci and enables the user of the present method to take into account recombination frequencies to aid in deconvolving the genetic signal produced by the pooled DNA. In some embodiments, the genetic map distance information comprises a genetic map made publicly available through publication or one of the public databases commonly used in the art. For instance, exemplary soybean and maize genetic maps are available from the USDA affiliated Soybase Website and the Maize Genetics and Genomics Database, respectively. In other embodiments, the genetic map can be generated for a particular plant species using genetic mapping techniques well known in the art, such as those described for the maize genetic map in Ganal et al., (2011) Plos ONE 6:e28334, the content of which is incorporated herein by reference in its entirety. In yet other embodiments, genetic maps may be constructed by first creating a large recombinant population from a cross between two parent plants with contrasting genotypes for the markers in question. Then, all recombinants are genotyped for those markers and the recombination rates r_k are calculated as the number of recombinants with allele combinations different from those found in the parents. Finally, the recombination rates are converted to genetic map distances using the inverse of the Haldane equation (VIII):

$$d_k = -\frac{\ln(1 - 2r_k)}{2}$$

It should be understood that the present methods do not require that a genetic map be developed or obtained for any particular plant genotype so long as the genetic map is from the same plant species as the plant progeny being genotyped.

Therefore, once the inputs pertaining to the genotype data of the pooled progeny samples, the marker alleles of the parent plants, the pedigree relationship between the progeny plants and their respective ancestors, and the genetic map of the genome are collected and/or detected, in-silico deconvolution can be implemented to determine a probability of each possible genotype for at least one marker locus in one or more of the progeny plants. In a preferred embodiment, Hidden Markov Models are used to select the most probable genotype of each possible genotype for at least one marker locus in one or more of the progeny plants. In the most preferred embodiment, Hidden Markov Models are used generate posterior probabilities to determine a probability of each possible genotype for at least one marker locus in one or more of the progeny plants.

Hidden Markov Modeling in Probablistic In-Silico Deconvolution

The present methods utilize in-silico deconvolution to accurately recover the marker genotypes from a pooled DNA sample, wherein the pooled DNA sample comprises: 1) an admixture of genomic DNA samples isolated from each progeny produced by two or more different parental crosses; 2) genomic DNA extracted from tissue samples pooled from each progeny produced by two or more different parental crosses; or 3) genomic DNA extracted from an offspring of a progeny plant produced by a parental cross that is crossed to another progeny plant produced by a different parental cross. In each case, the methods of the present disclosure include a step of detecting in the pooled DNA sample at least one allele of one or more marker locus using the techniques described herein.

In one embodiment, each progeny plant is a doubled haploid (DH/H) from different controlled biparental breeding crosses. In another embodiment, the progeny plants are derived through less than one or one or more filial selfings. In some embodiments, the genotypes of interest in each of the parents are known. In preferred embodiments, each parent is a known, fixed genetic entity and genotyped with high density. This genetic structure can be exploited using the present methods to substantially increase genotyping efficiency. In a particular embodiment, provided herein is a method that comprises pooling genomic DNA samples isolated from two or more plant progeny produced from different parental breeding crosses, genotyping the pooled genomic DNA pool jointly, or simultaneously, and deconvoluting the genetic signal produced by the genotyping using in-silico deconvolution as will be described herein in detail.

Depicted in FIG. 1, is a schematic illustration of an exemplary method of simultaneous pooled genotyping as compared to standard genotyping protocols. As shown on the left, standard genotyping protocols require genotyping of each progeny plant. Thus, for two progeny plants, genomic DNA must be isolated and purified from each individual. Each genomic sample is then genotyped using any suitable genotyping technique known in the art. Shown on the right in FIG. 1 is an exemplary embodiment of the present method. In this embodiment, genomic DNA is extracted and purified from plant tissue pooled from two progeny plants. The genetic signal produced by the pooled genotyping is resolved via in-silico deconvolution to determine the genotype of each individual. Thus, the present methods provide efficiency gains that facilitate genotyping at a considerably larger scale as compared to conventional genotyping thereby enabling genomic selection. In preferred embodiments, probalistic in-silico deconvolution is utilized. In more preferred embodiments, the probalistic in-silico deconvolution implements a Hidden Markov Model (HMM). Probalistic in-silico deconvolution with an HMM will now be described in further detail.

Probabilistic in-silico deconvolution infers the marker genotypes of the pooled individuals (e.g., plant progeny) in reference to the set of their direct ancestors (e.g., the parents of the breeding crosses that produced the plant progeny). In a particular embodiment, the present method comprises a deconvolution algorithm that includes, as input, four pieces of information:
 1. the genotype data of the DNA pool;
 2. the marker genotypes of the ancestors (e.g., parent plants);
 3. the pedigree relationship between the pooled progeny plant DNA and the ancestors (e.g., parent plants); and
 4. the genetic map of the genome.

Given this information, in some embodiments, the algorithm is executed to calculate for each marker locus in the genome the posterior inheritance probabilities of the pooled individuals vis-à-vis the ancestors. These probabilities are then used to infer the marker genotypes of the pooled individuals. In some embodiments, the pooled individuals are progeny plants, each resulting from crossing a different pair of parent plants, wherein genomic DNA is isolated from each progeny plant and pooled to produce a pooled genomic DNA sample for genotyping. In other embodiments, the pooled individuals are progeny plants, each resulting from crossing a different pair of parent plants, wherein genomic DNA is isolated from tissue samples pooled from each progeny plant. In yet other embodiments, the pooled individuals are progeny plants, each resulting from crossing a different pair of parent plants, wherein the progeny plants are then crossed to produce an offspring from which genomic DNA is isolated to be used for genotyping. In such embodiments, the ancestors are parent plants that are crossed to produce the progeny plants. In some embodiments, progeny plants from two or more different parental crosses are genotyped according to the present methods. In other embodiments, progeny plants from three or more different parental crosses are genotyped according to the present methods. In yet other embodiments, progeny plants from four or more different parental crosses are genotyped according to the present methods. In particular aspects, genotyping is done on one or more marker loci. In preferred aspects, genotyping is done on two or more marker loci. In more preferred aspects, genotyping is done on three or more marker loci, e.g., 3, 4, 5, 6, 7, 8, 9, 10, 11, 12, 13, 14, 15, 16, 17, 18, 19, 20, 50, 100, 200, 300, 400, 500, 600, 700, 800, 900, 1,000, or more marker loci.

The dependence of the inheritance calculation on the four pieces of information listed above can be illustrated further. Without loss of generality, assume a case in which there are three genetically linked loci ($L_1$, $L_2$ and $L_3$) for a DNA pool involving two progeny plants ($P_1$ and $P_2$) from two parental breeding crosses ($I_1 \times I_2$ and $I_3 \times I_4$), and absence of genotype detection error in either the pool or the ancestors:

At the first locus ($L_1$) the genotype allele T has been detected in the pool and only ancestor $I_4$ carries that allele. In this case at least one individual in the pool must inherit from ancestor $I_4$. This inference is made based on knowledge of both the genotype data of the pool and the ancestor genotype data.

If there is no pedigree information, then the probability of inheriting from founder $I_4$ will be spread evenly across all pooled individuals. However, the pedigree information indicates that only progeny $P_2$ could possibly descend from $I_4$. Thus, progeny $P_2$ must carry the T allele with probability of 100%. All other progenies in the pool consequently have a zero probability of carrying this allele. This inference is enabled by the pedigree relationship. A similar reasoning can be applied to show that progeny $P_1$ must have inherited allele A at locus $L_3$ from ancestor $I_2$.

At locus $L_2$ the pedigree and genotyping information alone is inconclusive, because both detected alleles can be traced to multiple ancestors and there are two possible inheritance patterns of the progenies that would give rise to the same observed pool genotype (either $I_1$ and $I_4$ or $I_2$ and $I_3$). However, it can be shown that by combining all aforementioned sources of information we can still calculate genotype probabilities and hence predict which progeny carries which allele. In the current case, the neighboring markers (ordered by the genetic map) indicate that the $I_1$ and $I_4$ inheritance pattern at $L_2$ requires a recombination event between loci $L_2$ and $L_3$, which is less likely than the recombination event between loci $L_1$ and $L_2$, which is required by the $I_2$ and $I_3$ pattern, thereby reducing the probability of the former.

The simple example from above shows how inconclusive cases can be resolved by collectively weighing information from the genetic map, the genotypes at neighboring markers and the pedigree information. For a genome and marker coverage of standard size, this can potentially involve a prohibitively large number of calculations, especially if genotyping errors are modeled. If all of the pool's direct ancestors are present in the ancestor set and the pedigree information fully describes all relationships between the ancestors and offspring (including the types of crosses carried out), then the inheritance of the ancestral genotypes along the genomes of the pooled individuals fulfills the requirements of an HMM. Alternatively, if one or more of these parameters are unknown, it is possible to train the HMM using multiple pooled genotypes from the same population.

The HMM incorporates the four pieces of information outlined above in the form of two matrices: the first matrix is referred to herein as the transition matrix, while the second matrix is referred to herein as the emission matrix. The transition matrix provides the probabilities that the pattern of inheritance at the previous locus can result in the pattern of inheritance at the current locus. These probabilities are a function of both the pedigree relationship information and the genetic map distance information. The emission matrix provides the probabilities that an observed genotype of the pool could be produced by each permutation of inheritance from the ancestors. This matrix incorporates the genotype information, and can be further simplified by pedigree information. Algorithms for HMMs operate on the emission and transition matrices to efficiently calculate the probabilities that the pooled individuals inherited each locus from each of the possible ancestors. These algorithms run efficiently even when there are a large number of marker loci and multiple ancestors. In cases where the pedigree is not fully known, the use of an HMM is not appropriate. Inference is still possible, but will require the use of more intensive computational techniques and likely a larger set of marker loci to achieve the same accuracy.

Probabilistic deconvolution, as described herein, makes optimal use of the four sources of information available routinely within commercial breeding programs. However, other in-silico deconvolution methods could be used as well, such as computational haplotype phasing described in Browning and Browning (2011) Nat. Rev. Genet. 122:703-714, the content of which is incorporated herein by reference in its entirety.

The HMM can be implemented with the forward-backward algorithm as described in Rabiner (1989) Proc. IEEE 77:257-286, the content of which is incorporated herein by reference in its entirety. Given a locus k, with an emission matrix $E_k$, a transition matrix $T_k$, and a vector of forward probabilities from the previous calculation (henceforth denoted as $f_{k-1}$), the forward pass is:

$$f_k = (T'_k f_{k-1}) \circ E_{k[m,]} \quad (I)$$

where [m, ] specifies the row of the emission matrix for the observed genotype m (e.g., A/A), "$\circ$" refers to element-wise multiplication. In some embodiments, equation (I) is modified to include a normalization constant $c_k$. Thus, equation (I) then becomes:

$$f_k = c_k^{-1}(T'_k f_{k-1}) \circ E_{k[m,]} \quad (II)$$

Where the normalization constant $c_k$ is equal to:

$$c_k = ((T'_k f_{k-1}) \circ E_{k[m,]})'1 \quad (III)$$

In some embodiments, the backward algorithm then is:

$$b_k = T'_k(b_{k+1} \circ E_{k[m,]}) \quad (IV)$$

where $b_k$ indicates the vector of backward probabilities. In some embodiments, equation (IV) is modified to include a normalization constant $\alpha_k$. Thus, equation (IV) then becomes:

$$b_k = \alpha_k^{-1} T'_k(b_{k+1} \circ E_{k[m,]}) \quad (V)$$

and $\alpha_k$ is similarly defined as $c_k$ where:

$$\alpha_k = (T = _k(b_{k+1} \circ E_{k[m,]}))'1 \quad (VI)$$

The initial vector of forward probabilities $f_0$, which is used when k=1, corresponds to the prior probabilities for the crosses involved in the pool. For instance, for a 2W pool of $F_1$ derived DH/H lines $f_0$=[0.25 0.25 0.25 0.25]' (i.e., the products of the expected parental genome contributions to the crosses, which are all equal to 0.5 in the case of $F_1$ crosses), the initial $b_{M+1}$, where M is the number of markers, for the backward pass is always [1 1 1 1]' (i.e., a vector of appropriate dimensions filled with 1's).

The forward pass is executed from k=1 to k=M and the backward pass from k=M to k=1. The posterior ancestral inheritance probabilities at locus k are then obtained by calculating:

$$p_k = (f_k \circ b_{k+1})([f_k \circ b_{k+1}]'1)^{-1} \quad (VII)$$

Depicted in FIG. 2 is a non-limiting exemplary embodiment of the present methods. Shown in FIG. 2 are parent plants, $I_1$, $I_2$, $I_3$, and $I_4$, which were crossed in two parental crosses $I_1/I_2$ and $I_3/I_4$. In this embodiment, the genotypes of the parent plants (i.e., ancestors) at the marker loci designated $L_1$, $L_2$, and $L_3$ are known. The allele calls for each parent and the pedigree relationships between the parent plants and progeny plants $P_1$ and $P_2$ are depicted. As shown in FIG. 2, progeny plants $P_1$ and $P_2$ are the offspring of parental crosses $I_1/I_2$ and $I_3/I_4$, respectively. While FIG. 2 reveals that progeny $P_1$ received marker alleles from parent plant $I_2$ at all three loci and progeny $P_2$ has received the marker allele at $L_1$ from parent plant $I_4$ and the marker alleles at loci $L_2$ and $L_3$ from parent plant $I_3$, it should be understood that this information is not known prior to the in-silico deconvolution step. In this embodiment, the progeny plants are not genotyped individually, but rather genomic DNA is isolated from each of the progeny plants and pooled to produce a pooled progeny genomic DNA. Alternatively, the pooled DNA sample is extracted from a pooled tissue sample. The pooled progeny DNA is then genotyped using any suitable genotyping technique. The forward-backward HMM can then be implemented to deconvolve the genotypes of $P_1$ and $P_2$ at marker loci $L_1$, $L_2$, and $L_3$.

The transition matrix $T_k$ for locus k describes the conditional probabilities that the pattern of inheritance at locus k-1 will result in a particular inheritance pattern at locus k. For example, it describes the probability that the pooled individuals inherited from ancestors $I_1$ and $I_3$ at locus $L_2$, conditional on them inheriting from $I_2$ and $I_3$ at locus $L_1$. In general, $T_k$ for a 2W pool is (outside labels not part of computation):

$$T_k = \begin{array}{c} I_1 - I_3 \\ I_1 - I_4 \\ I_2 - I_3 \\ I_2 - I_4 \end{array} \begin{bmatrix} (1-r_k)^2 & r_k(1-r_k) & r_k(1-r_k) & r_k^2 \\ r_k(1-r_k) & (1-r_k)^2 & r_k^2 & r_k(1-r_k) \\ r_k(1-r_k) & r_k^2 & (1-r_k)^2 & r_k(1-r_k) \\ r_k^2 & r_k(1-r_k) & r_k(1-r_k) & (1-r_k)^2 \end{bmatrix}$$

where $r_k$ is the recombination frequency between loci k and k-1. The recombination frequency can be calculated with the mapping function of Haldane (see Haldane (1919) J. Genet. 8:299-309, the content of which is incorporated herein by reference in its entirety) from the genetic map distance between two marker loci ($d_k$, in Morgans) as:

$$r_k = \frac{1 - e^{-2d_k}}{2} \quad \text{(VIII)}$$

In the exemplary embodiments shown in FIG. 2, the distance between locus $L_2$ and $L_1$ is 0.10 and that $L_3$ and $L_2$ is 0.05, which translates to $r_2=0.091$ and $r_3=0.048$. Because locus $L_1$ is located at the start of the chromosome and is hence not linked to any previous locus, $r_1=0.500$. Other mapping functions could have been used (e.g., Kosambi, (1943) Ann. Eugen. 12: 172-175, the content of which is incorporated herein by reference in its entirety). Substituting these values for $r_k$ gives the following transition matrices for the three loci (small discrepancies are possible due to rounding error).

$$T_1 = \begin{array}{c} I_1 - I_3 \\ I_1 - I_4 \\ I_2 - I_3 \\ I_2 - I_4 \end{array} \begin{bmatrix} 0.250 & 0.250 & 0.250 & 0.250 \\ 0.250 & 0.250 & 0.250 & 0.250 \\ 0.250 & 0.250 & 0.250 & 0.250 \\ 0.250 & 0.250 & 0.250 & 0.250 \end{bmatrix}$$

$$T_2 = \begin{array}{c} I_1 - I_3 \\ I_1 - I_4 \\ I_2 - I_3 \\ I_2 - I_4 \end{array} \begin{bmatrix} 0.827 & 0.082 & 0.082 & 0.008 \\ 0.082 & 0.827 & 0.008 & 0.082 \\ 0.082 & 0.008 & 0.827 & 0.082 \\ 0.008 & 0.082 & 0.082 & 0.827 \end{bmatrix}$$

$$T_3 = \begin{array}{c} I_1 - I_3 \\ I_1 - I_4 \\ I_2 - I_3 \\ I_2 - I_4 \end{array} \begin{bmatrix} 0.907 & 0.045 & 0.045 & 0.002 \\ 0.045 & 0.907 & 0.002 & 0.045 \\ 0.045 & 0.002 & 0.907 & 0.045 \\ 0.002 & 0.045 & 0.045 & 0.907 \end{bmatrix}$$

By adapting the transition matrix and the prior forward probabilities $f_0$, the HMM can be extended to cross types other than $F_1$ derived DH/H. For instance, in some embodiments, the transition matrix for a pool between two haploid or doubled haploid progeny plants that were derived from a backcross one (BC$_1$) generation, with $R_1$ and $D_1$ being the recurrent and donor parents of the first breeding cross and $R_2$ and $D_2$ those of the second breeding cross:

$$T_k = \begin{array}{c} R_1 - R_2 \\ R_1 - D_2 \\ D_1 - R_2 \\ D_1 - D_2 \end{array} \begin{bmatrix} \left(\frac{2}{3}\left(1+\frac{1}{2}(1-r_k)^2\right)\right)^2 & \frac{2}{3}\left(1+\frac{1}{2}(1-r_k)^2\right)\cdot\frac{1}{3}(2r_k-r_k^2) & \frac{2}{3}\left(1+\frac{1}{2}(1-r_k)^2\right)\cdot\frac{1}{3}(2r_k-r_k^2) & \left(\frac{1}{3}(2r_k-r_k^2)\right)^2 \\ \frac{2}{3}\left(1+\frac{1}{2}(1-r_k)^2\right)\cdot(2r_k-r_k^2) & \frac{2}{3}\left(1+\frac{1}{2}(1-r_k)^2\right)\cdot(1-r_k)^2 & \frac{1}{3}(2r_k-r_k^2) & \frac{1}{3}(2r_k-r_k^2)\cdot(1-r_k)^2 \\ (2r_k-r_k^2)\cdot\frac{2}{3}\left(1+\frac{1}{2}(1-r_k)^2\right) & \frac{1}{3}(2r_k-r_k^2)^2 & (1-r_k)^2\cdot\frac{2}{3}\left(1+\frac{1}{2}(1-r_k)^2\right) & (1-r_k)^2\cdot\frac{1}{3}(2r_k-r_k^2) \\ (2r_k-r_k^2)^2 & (2r_k-r_k^2)\cdot(1-r_k)^2 & (1-r_k)^2\cdot(2r_k-r_k^2) & (1-r_k)^4 \end{bmatrix}$$

For the same cross type, $f_0 = [0.5625 \ 0.1875 \ 0.1875 \ 0.0625]'$. With similar adaptations, the method can be extended to other cross types, including, but not limited to, DH/H or filial individuals from advanced backcross generations (BC$_2$, BC$_3$, etc.), individuals derived through filial selfing (e.g., F$_2$, F$_3$ individuals), DH/H derived from more advanced filial generations (F$_2$, F$_3$, etc.) and DH/H or filial individuals from breeding crosses involving more than 2 parents (e.g., three- or four-way crosses). It should be appreciated that the transition matrix formula can be readily adapted to any type of breeding cross in view of the present disclosure and is well within ordinary skill in the art.

Returning to the exemplary embodiment shown in FIG. 2, the emission matrix $E_k$ for locus k describes the probabilities of an observed marker genotype conditional on the ancestral inheritance pattern of the pool. For instance, conditional on the pool inheriting from $I_1$ and $I_3$ at locus $L_1$, the probability of observing the A/A genotype is one and that for the A/T and T/T genotypes zero. Conditional on the pool inheriting from $I_1$ and $I_4$, the probabilities of observing the A/A or T/T genotypes are zero while the probability for the A/T genotype is one. Applying this rationale to all loci and inheritance patterns yields the following three emission matrices (labels not part of computation):

$$E_1 = \begin{array}{c} A/A \\ A/T \\ T/T \end{array} \begin{bmatrix} I_1-I_3 & I_1-I_4 & I_2-I_3 & I_2-I_4 \\ 1 & 0 & 1 & 0 \\ 0 & 1 & 0 & 1 \\ 0 & 0 & 0 & 0 \end{bmatrix}$$

$$E_1 = \begin{array}{c} C/C \\ C/T \\ T/T \end{array} \begin{bmatrix} I_1-I_3 & I_1-I_4 & I_2-I_3 & I_2-I_4 \\ 1 & 1 & 1 & 0 \\ 0 & 0 & 1 & 0 \\ 0 & 0 & 0 & 1 \end{bmatrix}$$

$$E_1 = \begin{array}{c} G/G \\ G/A \\ A/A \end{array} \begin{bmatrix} I_1-I_3 & I_1-I_4 & I_2-I_3 & I_2-I_4 \\ 1 & 1 & 0 & 0 \\ 0 & 0 & 1 & 1 \\ 0 & 0 & 0 & 0 \end{bmatrix}$$

In this embodiment depicted in FIG. 2, genotyping errors were assumed to be absent. Alternatively, if genotyping errors are considered, the values in the matrices would slightly deviate from 1 and 0, to reflect that, for example, a pool genotype of A/T has a slight chance of being observed even when both ancestors are homozygous for the A allele. To accommodate missing genotypes, a fourth row filled with 1's can be added to the matrices.

With the transition and emission matrices in place, the forward and backward probabilities $f_k$ and $b_k$ are then calculated. Starting at k=1, the forward probabilities according to equation (II) are:

$$f_1 = c_1^{-1}(T_1'f_0) \circ E_{1[A/T,]}$$
$$= (0.000 \ 0.500 \ 0.000 \ 0.500)'$$

-continued $$f_2 = c_2^{-1}(T_2' f_1) \circ E_{2[C/T,]}$$
$$= (0.000 \quad 0.909 \quad 0.091 \quad 0.000)'$$

$$f_3 = c_3^{-1}(T_3' f_2) \circ E_{3[G/A,]}$$
$$= (0.000 \quad 0.000 \quad 0.650 \quad 0.350)'$$

and starting from k=3, the backward probabilities according to equation (V) are:

$$b_3 = a_3^{-1} T_3'(b_4 \circ E_{3[G/A,]})$$
$$= (0.024 \quad 0.024 \quad 0.476 \quad 0.476)'$$

$$b_2 = a_2^{-1} T_2'(b_3 \circ E_{2[C/T,]})$$
$$= (0.082 \quad 0.047 \quad 0.788 \quad 0.082)'$$

$$b_1 = a_1^{-1} T_1'(b_2 \circ E_{1[A/T,]})$$
$$= (0.250 \quad 0.250 \quad 0.250 \quad 0.250)'$$

Finally, after applying equation (VII) and arranging the results in a matrix the posterior ancestral inheritance probabilities $p_k$ are obtained (see FIG. 2) as follows:

$$p_k = \begin{matrix} & I_1-I_3 & I_1-I_4 & I_2-I_3 & I_2-I_4 \\ L_1 & 0.000 & 0.364 & 0.000 & 0.636 \\ L_2 & 0.000 & 0.334 & 0.666 & 0.000 \\ L_3 & 0.000 & 0.000 & 0.650 & 0.350 \end{matrix}$$

In the embodiment shown in FIG. 2, the posterior probability that the pooled DH/H inherited from ancestors $I_2$ and $I_3$ at locus $L_2$ is ⅔ and that they inherited from ancestors $I_1$ and $I_4$ equal to ⅓. Inheritance from $I_1$ and $I_3$ or $I_2$ and $I_4$ has zero probability because observing the C/T pool genotype is impossible when both ancestors are homozygous for the same allele, in the absence of genotyping error. The pedigree information that progeny $P_1$ inherited from either $I_1$ or $I_2$ and progeny $P_2$ from either $I_3$ or $I_4$ is known. Therefore, the conclusion is made that the most probable marker genotype for progeny $P_1$ at locus $L_2$ is T and for $P_2$ it is C.

In some embodiments, deconvolution with Hidden Markov Modeling can be expressed on the scale of the natural logarithm (base e). When expressed on the scale of base e, the log forward probabilities become:

$$\ln(f_{k[i]}) = \ln \Sigma_{j=1}[\ln(T_{k[j,i]})*_{ln}\ln(f_{k-1[j]})]*_{ln}\ln(E_{k[m,i]}) \quad (IX)$$

the log backward probabilities become:

$$\ln(b_{k[i]}) = \ln \Sigma_{j=1}\{\ln(T_{k[i,j]})*_{ln}[\ln(b_{k+1[j]})*_{ln}\ln(E_{k[m,j]})]\} \quad (X)$$

and the log posterior ancestral probabilities become:

$$\ln(p_{k[i]}) = -\{\ln \Sigma_{j=1}[\ln(f_{k[j]})*_{ln}\ln(b_{k+1[j]})]\}*_{ln}[\ln(f_{k[i]}) \\ *_{ln}\ln(b_{k+1[i]})] \quad (XI)$$

where ln(x) is the natural logarithm of x, redefined to return $0_{ln}$ if x is extremely close or equal to 0, with $0_{ln}$ being any negative number for which $e^{0_{ln}} \approx 0$, e.g., $0_{ln} = -1000$. Further:

$$\ln \Sigma_{j=1}^{j=S} \ln(x_j) = (((\ln(x_1)+_{ln}\ln(x_2))+_{ln}\ln(x_3))+_{ln}\ln(x_S)) \quad (XII)$$

with the 'log sum' operator $+_{ln}$ defined as:

$$\ln(x) +_{ln} \ln(y) = \begin{cases} \ln(y), & \text{if } \ln(x) = 0_{ln} \\ \ln(x), & \text{if } \ln(y) = 0_{ln} \\ 0_{ln}, & \text{if } \ln(x) = \ln(y) = 0_{ln} \\ \text{else} \begin{cases} \ln(x) + \ln(1 + \exp\langle\ln(y)-\ln(x)\rangle), & \text{if } \ln(x) > \ln(y) \\ \ln(x) + \ln(1 + \exp\langle\ln(x)-\ln(y)\rangle), & \text{if } \ln(y) \geq \ln(x) \end{cases} \end{cases} \quad (XIII)$$

and the 'log product' operator $*_{ln}$ as:

$$\ln(x) *_{ln} \ln(y) = \begin{cases} 0_{ln}, & \text{if } \ln(x) = 0_{ln} \\ 0_{ln}, & \text{if } \ln(y) = 0_{ln} \\ \ln(x) + \ln(y), & \text{else} \end{cases} \quad (XIV)$$

For validation purposes and to assess the accuracy of the deconvolution process, the inferred marker genotypes obtained from the present methods can be compared with the true or observed marker scores of the pooled progeny plants. However, for many applications, such as whole genome prediction (see, e.g., Meuwissen et al., (2001) Genetics 157:1819-1829, the content of which is incorporated herein by reference in its entirety), the ancestral inheritance probabilities $p_k$ could be used directly.

Suitable Techniques for the Detection of Marker Alleles

In certain aspects described herein, the method of simultaneous pooled genotyping of two or more progeny plants includes a detecting step. For instance, in some embodiments, the detecting step comprises detecting in a pooled DNA sample at least one marker allele. In other embodiments, the ancestral or parent plants used in a parental breeding cross are genotyped and involves a detecting step where at least one marker allele in one or more parent plants is detected. In yet other embodiments, methods utilizing detection steps for both the parent plants as well as the progeny plants are provided. In such embodiments, the detection step comprises the detection of at least one allele of one or more marker loci in the parent plants and the progeny plant(s) produced by crossing the parent plants. While not intending to be limited to any particular embodiment, provided herein are exemplary detection methods suitable for use with the present methods.

In one embodiment, the method of detection comprises DNA sequencing of at least one marker loci in a parent plant and/or a progeny plant. As used herein, "sequencing" refers to sequencing methods for determining the order of nucleotides in a molecule of DNA. Any DNA sequencing method known in the art can be used in the methods provided herein. Non-limiting embodiments of DNA sequencing methods useful in the methods provided herein include Next Generation Sequencing (NGS) technologies, for example, as described in Egan et al., (2012) American Journal of Botany 99(2):175-185; genotyping by sequencing (GBS) methods, for example, as described in Elshire et al., (2011) PLoS ONE 6(5):e19379; Molecular Inversion Probe (MIP) genotyping, as described, for example, in Hardenbol et al., (2003) Nature Biotechnology 21(6):673-678; or high throughput genotyping by whole-genome resequencing, as described, for example in Huang et al., (2009) Genome Research 19:1068-1076. Each of the above references is incorporated by reference in its entirety herein. In some genotyping methods, the genotype is inferred by counts of alleles, for example, sequencing read counts to determine both the identity of the allele and its zygosity.

In other aspects, the detecting may comprise designing a primer or probe that is complementary or partially complementary to at least a portion of the genomic DNA encompassing the marker locus and capable of specifically hybridizing to the marker locus of interest under at least moderately stringent conditions. In such aspects, the primer or probe optionally comprises a detectable label. Genomic DNA may be extracted from plant material using any suitable technique in the art, e.g., the CTAB (cetyltriethylammonium bromide, Sigma H5882) method described by Stacey & Isaac (1994), the content of which is incorporated herein by reference in its entirety. Detecting may comprise isolating nucleic acids, amplifying the genomic DNA encompassing the marker locus or a portion of the genomic DNA encompassing the marker locus and detecting the resulting amplified marker amplicon. In some embodiments, the amplifying comprises admixing an amplification primer or amplification primer pair, and optionally at least one nucleic acid probe, with a nucleic acid isolated from the soybean plant or soybean germplasm, wherein the primer or primer pair and optional probe is complementary or partially complementary to at least a portion of the genomic DNA encompassing the marker locus and is capable of initiating DNA polymerization by a DNA polymerase using the nucleic acid as a template; and, extending the primer or primer pair in a DNA polymerization reaction comprising a DNA polymerase and a template nucleic acid to generate at least one amplicon. In particular embodiments, the detection comprises real time PCR analysis.

In some embodiments, molecular markers are detected using a suitable amplification-based detection method. Typical amplification methods include various polymerase based replication methods, including the polymerase chain reaction (PCR), ligase mediated methods, such as the ligase chain reaction (LCR), and RNA polymerase based amplification (e.g., by transcription) methods. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage & Caruthers (1981) Tetrahedron Letts 22:1859-1862, e.g., using a commercially available automated synthesizer, e.g., as described in Needham-VanDevanter et al. (1984) Nucl Acids Res 12:6159-6168, the contents of each are incorporated herein by reference in their entireties. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair, or probe. For example, primers can be designed using any suitable software program, such as LASERGENE® or Primer3.

The primers are not limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length, or alternatively, at least 300 nucleotides in length, or alternatively, at least 400 nucleotides in length, or alternatively, at least 500 nucleotides in length, or alternatively, at least 1000 nucleotides in length, or alternatively, at least 2000 nucleotides in length or more.

PCR, RT-PCR, and LCR are common amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous references, such as Mullis et al. (1987) U.S. Pat. No. 4,683,202; Arnheim & Levinson (1990) C&EN 36-47; Kwoh et al. (1989) Proc Natl Acad Sci USA 86:1173; Guatelli et al. (1990) Proc Natl Acad Sci USA 87:1874; Lomell et al. (1989) J Clin Chem 35:1826; Landegren et al. (1988) Science 241:1077-1080; Van Brunt (1990) Biotechnology 8:291-294; Wu & Wallace (1989) Gene 4:560; Barringer et al. (1990) Gene 89:117; and Sooknanan & Malek (1995) Biotechnology 13:563-564, the contents of each are incorporated herein by reference in their entireties.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype alleles, such as SNP alleles, are provided. Real-time amplification assays, including molecular beacon or TAQMAN® based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain embodiments, each allele-specific probe for a certain SNP locus is 13-18 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

In certain embodiments, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and their corresponding detection strategies can be found, e.g., in Haugland (1996) *Handbook of Fluorescent Probes and Research Chemicals Sixth Edition* by Molecular Probes, Inc. (Eugene, Oreg.); or Haugland (2001) *Handbook of Fluorescent Probes and Research Chemicals Eighth Edition* by Molecular Probes, Inc. (Eugene, Oreg.), the contents of each are incorporated herein by reference in their entireties.

Detectable labels may also include reporter-quencher pairs, such as are employed in Molecular Beacon and TAQMAN® probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent. Generally, whether the quencher is fluorescent or simply releases the transferred energy from the reporter by nonradiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules*, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland (2001) *Handbook of Fluorescent Probes and Research Chemicals Eighth Edition* by Molecular Probes, Inc. (Eugene, Oreg.), the content of which is incorporated herein by reference.

In certain embodiments, reporter-quencher pairs are selected from xanthene dyes including fluorescein and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters is the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-i sothiocyanatoacridine; N-(p-(2-benzoxazolyl)phenyl)maleimide; benzoxadiazoles; stilbenes; pyrenes and the like. In certain other embodiments, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif, QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TAQMAN® probes. A molecular beacon (MB) is an oligonucleotide that, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone et al. (1995) Nucl Acids Res 26:2150-2155; Tyagi & Kramer (1996) Nat Biotechnol 14:303-308; Blok & Kramer (1997) Mol Cell Probes 11:187-194; Hsuih et al. (1997) J Clin Microbiol 34:501-507; Kostrikis et al. (1998) Science 279:1228-1229; Sokol et al. (1998) Proc Natl Acad Sci USA 95:11538-11543; Tyagi et al. (1998) Nat Biotechnol 16:49-53; Bonnet et al. (1999) Proc Natl Acad Sci USA 96:6171-6176; Fang et al. (1999) J Am Chem Soc 121:2921-2922; Marras et al. (1999) Genet Anal Biomol Eng 14:151-156; and, Vet et al. (1999) Proc Natl Acad Sci USA 96:6394-6399. Additional details regarding MB construction and use are also found in the patent literature, e.g., U.S. Pat. Nos. 5,925,517; 6,150,097; and 6,037,130. Each of the above references are incorporated herein by reference in their entireties.

Another real-time detection method is the 5'-exonuclease detection method, also called the TAQMAN® assay, as set forth in U.S. Pat. Nos. 5,804,375; 5,538,848; 5,487,972; and 5,210,015, the contents of each are hereby incorporated by reference in their entireties. In the TAQMAN® assay, a modified probe, typically 10-30 nucleotides in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are typically attached to the probe within a few nucleotides of one another, usually within 30 nucleotides of one another, or within 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

One embodiment of a suitable real-time detection technique that does not use a separate probe that binds intermediate to the two primers is the KASPar detection system/method, which is well known in the art. In KASPar, two allele specific primers are designed such that the 3' nucleotide of each primer hybridizes to the polymorphic base. For example, if the SNP is an A/C polymorphism, one of the primers would have an "A" in the 3' position, while the other primer would have a "C" in the 3' position. Each of these two allele specific primers also has a unique tail sequence on the 5' end of the primer. A common reverse primer is employed that amplifies in conjunction with either of the two allele specific primers. Two 5' fluor-labeled reporter oligos are also included in the reaction mix, one designed to interact with each of the unique tail sequences of the allele-specific primers. Lastly, one quencher oligo is included for each of the two reporter oligos, the quencher oligo being complementary to the reporter oligo and being able to quench the fluor signal when bound to the reporter oligo. During PCR, the allele-specific primers and reverse primers bind to complementary DNA, allowing amplification of the amplicon to take place. During a subsequent cycle, a complementary nucleic acid strand containing a sequence complementary to the unique tail sequence of the allele-specific primer is created. In a further cycle, the reporter oligo interacts with this complementary tail sequence, acting as a labeled primer. Thus, the product created from this cycle of PCR is a fluorescently-labeled nucleic acid strand. Because the label incorporated into this amplification product is specific to the allele specific primer that resulted in the amplification, detecting the specific fluor presenting a signal can be used to determine the SNP allele that was present in the sample.

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook; *Current Protocols in Molecular Biology*, F. M. Ausubel et al., eds., Current Protocols, a joint venture between Greene Publishing Associates, Inc. and John Wiley & Sons, Inc., (supplemented through 2002); and, *PCR Protocols A Guide to Methods and Applications* (Innis et al., eds) Academic Press Inc. San Diego, Calif. (1990). Additional details regarding detection of nucleic acids in plants can also be found, e.g., in *Plant Molecular Biology* (1993) Croy (ed.) BIOS Scientific Publishers, Inc. Each of the above references are incorporated herein by reference in their entireties.

Other techniques for detecting SNPs can also be employed, such as allele specific hybridization (ASH) or nucleic acid sequencing techniques. ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Isolated polynucleotide or fragments thereof, e.g., a primers and/or probe, are capable of specifically hybridizing to other nucleic acid molecules under appropriate conditions. In some embodiments, the nucleic acid molecules comprise any of the marker loci of the present invention. It will be appreciated that suitable primers and probes to be used can be designed using any suitable method. It is not intended to be limited to any particular primer, primer pair or probe. For example, primers or probes can be designed using any suitable software program, such as LASERGENE® or Primer3. In another aspect, the primers and probes of the present invention include nucleic acid molecules that hybridize, for example, under high or low stringency, substantially homologous sequences, or that have both to these molecules. Conventional stringency conditions are described by Sambrook, and by Haymes et al. In: Nucleic Acid Hybridization, A Practical Approach, IRL Press, Washington, D.C. (1985), the contents of each are incorporated herein by reference in their entireties. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed. Appropriate stringency conditions that promote DNA hybridization are known to those skilled in the art or can be found in Current Protocols in Molecular Biology, John Wiley & Sons, N.Y., 1989, 6.3.1-6.3.6, the content of which is incorporated herein by reference in its entirety.

Typically, stringent conditions will be those in which the salt concentration is less than about 1.5 M Na ion, typically about 0.01 to about 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the thermal melting point (Tm) can be approximated from the equation of Meinkoth et al., *Anal. Biochem.* 138:267-284 (1984), the content of which is incorporated herein by reference in its entirety: Tm=81.5° C.+16.6 (log M) 4-0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm hybridization and/or wash conditions can be adjusted to hybridize to sequences of the desired identity. For example, if sequences with ≥90% identity are sought, the Tm can be decreased 10° C. Generally, stringent conditions are selected to be about 5° C. lower than Tm for the specific sequence and its complement at a defined ionic strength and pH. However, severely stringent conditions can utilize a hybridization and/or wash at 1, 2, 3, or 4° C. lower than the Tm; moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm. Using the equation, hybridization and wash compositions, and desired Tm those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier, New York (1993); and Current Protocols in Molecular Biology, Chapter 2, Ausubel et al., Eds., Greene Publishing and Wiley-Inter-science, New York (1995), the content of each are incorporated herein by reference in their entireties. Hybridization and/or wash conditions can be applied for at least 10, 30, 60, 90, 120, or 240 minutes.

Detection of Marker Loci Associated with One or More Phenotypes

It is a further object of this disclosure to provide for a method of simultaneous pooled genotyping two or more progeny plants for marker loci associated with one or more phenotypes. In a certain aspect, a method of simultaneous pooled genotyping two or more progeny plants, each resulting from crossing a different pair of parent plants is provided and includes a detection step comprising one or more isolated polynucleotides capable of hybridizing with a favorable allele of a marker locus associated with at least one phenotype selected from the group consisting of yield, leaf angle, anthesis-silking interval, staygreen duration, early growth rate, overall growth rate, growth pattern, maximum biomass, total biomass, nitrogen use efficiency, water use efficiency, tocol content, oleic acid content, phytic acid content, amino acid composition, oil quantity or quality, energy availability, digestibility, fatty acid composition, a pathogen defense mechanism, lysine and sulfur levels, starch synthesis, disease resistance, herbicide resistance, male sterility, plant vigor, nutrient content, hemicellulose content, cellulose production, cold tolerance, salt tolerance, heat tolerance, drought tolerance, grain moisture content, stalk lodging, root lodging, root pulling resistance, stand establishment, emergence, midsilk, test weight, protein content, starch percentage, relative maturity, plant height, seed size, heading date, resistance to insects, disease resistance, brittle snap, stalk breakage, resistance to fungus, seed moisture, head shape, hullability, seedling vigor, beginning to bloom date, maturity date, seed shatter, winter survival, fiber strength, ear height, plant barrenness, seed number, seed weight, and color grade. In certain embodiments, the isolated polynucleotide is a primer or probe. In a particular embodiment, the method further comprises detecting the presence of the hybridized polynucleotide in one or more of the genomic DNA samples or a pooled genomic DNA sample as an indication of a progeny plant with a favorable allele of a marker locus associated with yield, leaf angle, anthesis-silking interval, staygreen duration, early growth rate, overall growth rate, growth pattern, maximum biomass, total biomass, nitrogen use efficiency, water use efficiency, tocol content, oleic acid content, phytic acid content, amino acid composition, oil quantity or quality, energy availability, digestibility, fatty acid composition, a pathogen defense mechanism, lysine and sulfur levels, starch synthesis, disease resistance, herbicide resistance, male sterility, plant vigor, nutrient content, hemicellulose content, cellulose production, cold tolerance, salt tolerance, heat tolerance, drought tolerance, grain moisture content, stalk lodging, root lodging, root pulling resistance, stand establishment, emergence, midsilk, test weight, protein content, starch percentage, relative maturity, plant height, seed size, heading date, resistance to insects, disease resistance, brittle snap, stalk breakage, resistance to fungus, seed moisture, head shape, hullability, seedling vigor, beginning to bloom date, maturity date, seed shatter, winter survival, fiber strength, ear height, plant barrenness, seed number, seed weight, and/or color grade. In other embodiments, a progeny plant or germplasm thereof for which the presence of the hybridized polynucleotide is detected is crossed to another plant, such as a recurrent parent, to produce a population of progeny plant germplasm. In such embodiments, the progeny plant germplasm can be genotyped for the presence of a marker allele favorable for one or more of the above-described phenotypes using the detection methods described herein.

In addition to the phenotypes described above, the marker loci detected in the present methods are associated with one or more other phenotypes of interest including but not limited to improved resistance to one or more ALS-inhibiting herbicides, a hydroxyphenylpyruvatedioxygenase inhibitor, a phosphanoglycine (including but not limited to a glyphosate), a sulfonamide, an imidazolinone, a bialaphos, a phosphinothricin, a metribuzin, a mesotrione, an isoxaflutole, an azafenidin, a butafenacil, a sulfosate, a glufosinate, a dicamba, a 2,4-D, and a protox inhibitor. In some embodiments, one or more of the marker loci detected by the present methods are associated with one or more phenotypes selected from the group consisting of extended reproductive growth stage, early flowering, drought tolerance, stress tolerance, disease resistance, herbicide resistance, enhanced yield, modified oil, modified protein, tolerance to chlorotic conditions, and insect resistance, or any combination thereof. In some embodiments, the trait is selected from the group consisting of charcoal rot drought complex resistance, Fusarium resistance, Phytophthora resistance, stem canker resistance, sudden death syndrome resistance, Sclerotinia resistance, Cercospora resistance, anthracnose resistance, target spot resistance, frogeye leaf spot resistance, soybean cyst nematode resistance, root knot nematode resistance, rust resistance, high oleic content, low linolenic content, aphid resistance, stink bug resistance, and iron chlorosis deficiency tolerance, and any combination thereof. In some embodiments, one or more of the traits is conferred by one or more transgenes, by one or more native loci, or any combination thereof.

The present disclosure is illustrated by the following examples. The foregoing and following description and the various examples are not intended to be limiting but rather are illustrative of the described embodiments. Hence, it will be understood that the present disclosure is not limited to the specific details of these examples.

EXAMPLES

Example 1

Simulated Pools of Two DH/H (2W Pools)

Simultaneous pooled genotyping was demonstrated with simulated genotype data from maize and canola breeding crosses. The simulation included six two-DH (2W) pools of early maturity Stiff-Stalk Synthetic (SSS) and Non-Stiff Stalk (NSS) maize pedigrees and three 2W pools of B-line and R-line canola pedigrees (Table 1). For both crops the combinations included cases where all breeding crosses came from the same heterotic group as well as combinations of breeding crosses from different heterotic groups.

In this study, $I_1/I_2$ and $I_3/I_4$ represented two breeding crosses comprising the parental inbred lines $I_1$, $I_2$, $I_3$, and $I_4$. For each breeding cross, 250 $F_1$ DH/H plant progenies were generated using the observed single nucleotide polymorphism (SNP) genotypes of the parents and the corresponding genetic map. It was assumed, without loss of generality, that all markers were biallelic SNPs.

Meiosis was simulated according to the count-location model, which follows the assumptions of the Haldane mapping function as described in Karlin and Liberman (1978) Proc. Nat. Acad. Sci. 17:6332-6336, the content of which is hereby incorporated by reference in its entirety. Briefly, in the count-location model meiosis on a single chromosome was simulated by first drawing the number of crossovers from a Poisson distribution with rate parameter equal to the genetic length of the chromosome in Morgans. Then, the locations of the crossovers were drawn from a uniform distribution over the length of the chromosome. This process was then repeated for each chromosome. The simulations were carried out with the publicly available R package hypred (see Technow, "R Package hypred: Simulation of Genomic Data in Applied Genetics", package version 0.4 (2013), available at the Cran.R Project website, the content of which is hereby incorporated by reference in its entirety). However, any other meiosis simulation software could have been used (see, e.g., Maurer et al. (2008) Euphytica 161: 133-139; Voorrips and Maliepaard (2012) BMC Bioinformatics 13:248, the contents of each are hereby incorporated by reference in their entireties).

Finally, 250 DNA pools were generated by pairing the 250 progenies from $I_1/I_2$ with the 250 progenies from $I_3/I_4$ at random. A pool comprised one DH from each of the breeding crosses. The genotypes of the DNA pools were obtained from the paired DNA profiles (i.e., assigning a 0 or 2, depending on the allele, if the pairing resulted in a homozygous genotype or 1 if the pairing resulted in a heterozygous genotype).

Only markers polymorphic in at least one of the breeding crosses comprising a pool were considered. For monomorphic markers deconvolution is trivial. The HMI based in-silico deconvolution algorithm was run as described for each of the 250 2W pools of each breeding cross combination to infer the SNP genotypes of the pooled DH/H.

The deconvolution error rate (DER) was then assessed. In the case of 2W pools and in the absence of genotyping errors, deconvolution for markers polymorphic in only one of the breeding crosses comprising the pool is 100% accurate. This is because only one inheritance pattern can result in a heterozygous pool genotype as discussed elsewhere herein. The DER therefore had to be assessed only for markers polymorphic in both of the breeding crosses involved in the pool. Consequently, the DER was computed as the proportion of the markers polymorphic in both breeding crosses, for which the inferred marker genotype (the one most likely according to the HMM algorithm) did not match the observed marker genotype. This computation was done separately for each of the 250 pools. Note that deconvolution with the algorithm happens independently for each pool. The DER is therefore not dependent on the total number of pools considered. This will not be the case for deconvolution algorithms based on haplotype phasing as discussed in, for example, Browning and Browning (2011) Nat. Rev. Genet. 122:703-714, the content of which is hereby incorporated by reference in its entirety. The results of the simulated maize and canola 2W pools is shown in Table 1.

TABLE 1

Summary of results for simulated maize and canola 2W pools.

| | | Deconvolution Error Rate (%) | | |
| --- | --- | --- | --- | --- |
| Breeding cross combination | p (%) | 125 $M_G$ | 250 $M_G$ | 500 $M_G$ |
| Maize | | | | |
| (Variety M1/Variety M2) -- (Variety M3/Variety M4) | 14.8 | 2.9 | 1.7 | 0.5 |
| (Variety M5/Variety M3) -- (Variety M6/Variety M7) | 30.3 | 4.9 | 2.0 | 0.9 |
| (Variety M8/Variety M9) -- (Variety M10/Variety M11) | 16.0 | 3.3 | 1.3 | 0.4 |
| (Variety M12/Variety M13) -- (Variety M14/Variety M15) | 29.0 | 4.9 | 2.4 | 1.1 |
| (Variety M17/Variety M17) -- (Variety M18/Variety M19) | 8.60 | 2.9 | 0.7 | 0.2 |
| (Variety M1/Variety M20) -- (Variety M14/Variety M21) | 13.0 | 2.4 | 0.9 | 0.3 |

TABLE 1-continued

Summary of results for simulated maize and canola 2W pools.

| Breeding cross combination | p (%) | Deconvolution Error Rate (%) | | |
|---|---|---|---|---|
| | | 125 $M_G$ | 250 $M_G$ | 500 $M_G$ |
| Canola | | | | |
| (Variety C1/Variety C2) -- (Variety C3/Variety C4) | 26.8 | 4.1 | 1.2 | 0.3 |
| (Variety C5/Variety C6) -- (Variety C7/Variety C8) | 28.2 | 3.4 | 1.6 | 0.5 |
| (Variety C9/Variety C10) -- (Variety C11/Variety C12) | 27.6 | 2.8 | 1.0 | 0.3 |

A pool comprised one DH from each of the named breeding crosses. Reported are averages over all pools of a breeding cross combination. $M_G$ is number of genotyped markers and p is the proportion of markers polymorphic in both breeding crosses.

To assess the influence of the total number of markers on the DER, the number of markers was varied from a minimum of 100 to the maximum possible in steps of 25. For each breeding cross combination, the maximum was determined by the number of markers polymorphic in at least one of the breeding crosses. The markers were chosen at random, with the only constraint that each chromosome had to have at least 3 markers. For each of the 250 DNA pools of a breeding cross combination, the sampling of markers was done anew to incorporate the variability between marker sets into the overall uncertainty. This process was repeated for all of the six maize and three canola breeding cross combinations. The influence of the number of total markers genotyped on DER for the maize and canola breeding combinations is shown in FIGS. 3A-F and FIGS. 4A-C, respectively. As shown in FIGS. 3A-F, FIGS. 4A-C and Table 1, the DER decreased with increasing number of markers $M_G$ for all breeding combinations examined. For maize, the DER was higher for breeding cross combinations with a higher proportion p of doubly polymorphic markers. For combinations with p close to or lower than 15%, the DER was around 3% at $M_G$=125 and declined to values below 0.5% when $M_G$ was increased to 500. For pairs with p close to 30%, however, the DER at 125 $M_G$ was about 5% and around 1% at $M_G$ of 500. The DER of the canola breeding cross combinations was slightly lower than the DER in maize examples with similar p.

To assess the influence of the proportion of doubly polymorphic markers (p) to total number of markers on the DER, p was varied in 5% steps between 15% and 90%. Let $M_G$ denote the total number of markers for which the pool is genotyped. To arrive at the desired mix of markers, $pM_G$ and $(1-p)M_G$ markers were randomly sampled from the sets of markers polymorphic in both and only one of the breeding crosses, respectively. The value of $M_G$ was determined in such a way to obtain a target of $M_T$ polymorphic markers per breeding cross. The value of $M_G$ was calculated as $$M_G = \frac{M_T}{p + 0.5(1-p)} \quad (XV)$$

Figure 5A:
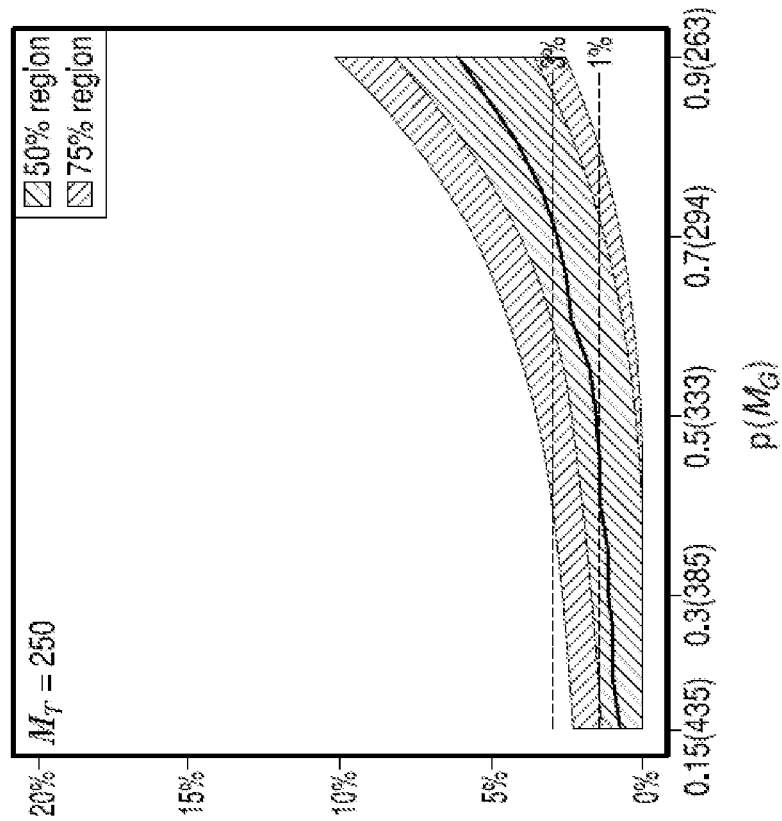
FIG. 5A depicts a graph showing the average DER for the maize parental cross Variety M5 x Variety M3 paired with the maize parental cross Variety M6 x Variety M7 as a function of the proportion of markers that are polymorphic in both pedigrees (p) and the target number of informative markers per pedigree ($M_T$). The number of informative markers are 100. The x-axis represents the total number of genotyped markers $M_G$, and the y-axis represents the DER. The shaded areas indicate the 50% and 75% central probability region.
Figure 5B:
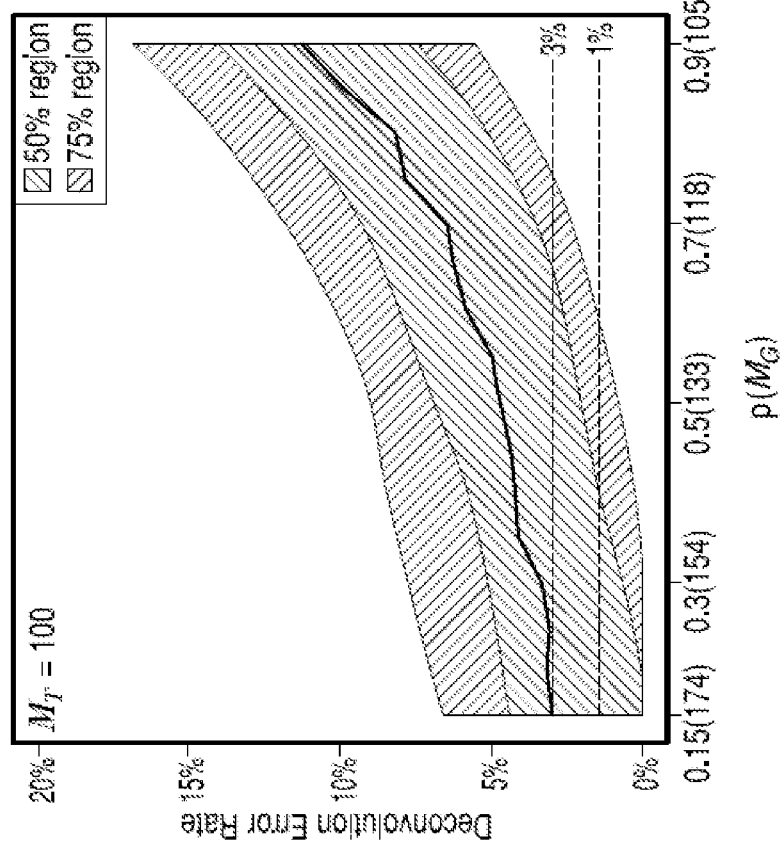
FIG. 5B depicts a graph showing the average DER for the maize parental cross Variety M5 x Variety M3 paired with the maize parental cross Variety M6 x Variety M7 as a function of the proportion of markers that are polymorphic in both pedigrees (p) and the target number of informative markers per pedigree ($M_T$). The number of informative markers are 250. The x-axis represents the total number of genotyped markers $M_G$, and the y-axis represents the DER. The shaded areas indicate the 50% and 75% central probability region.
Figure 5C:
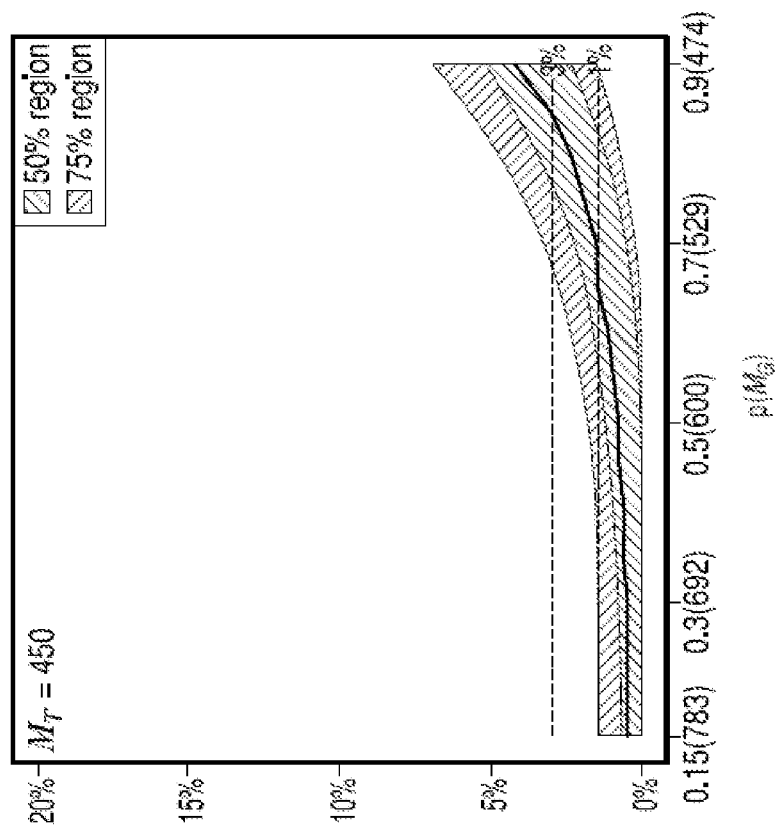
FIG. 5C depicts a graph showing the average DER for the maize parental cross Variety M5 x Variety M3 paired with the maize parental cross Variety M6 x Variety M7 as a function of the proportion of markers that are polymorphic in both pedigrees (p) and the target number of informative markers per pedigree ($M_T$). The number of informative markers are 450. The x-axis represents the total number of genotyped markers $M_G$, and the y-axis represents the DER. The shaded areas indicate the 50% and 75% central probability region.
Figure 6:
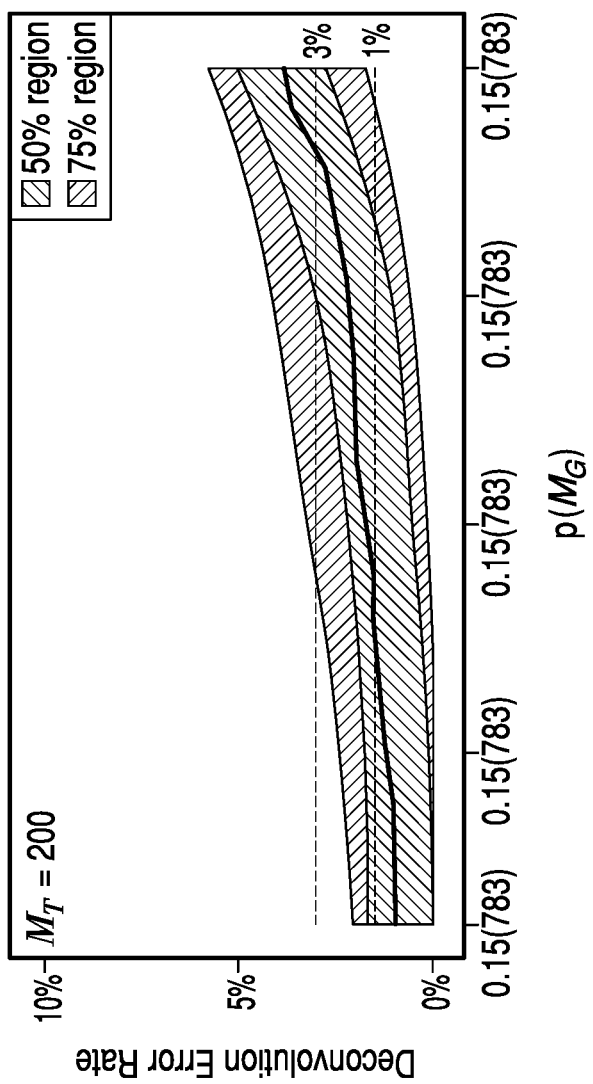
FIG. 6 depicts a graph showing the average DER for the canola parental cross Variety C5 x Variety C6 paired with the canola parental cross Variety C7 x Variety C8 as a function of the proportion of markers that are polymorphic in both pedigrees (p) and the target number of informative markers per pedigree ($M_T$). The x-axis represents the total number of genotyped markers is $M_G$, and the y-axis represents the DER. The shaded areas indicate the 50% and 75% central probability region.

For example, if $M_T$=100 polymorphic markers are desired for each breeding cross, then 154 markers have to be genotyped when p=0.3 and 118 when p=0.7. This analysis was done for the maize SSS breeding cross combination (Variety M5/Variety M3) with (Variety M6/Variety M7) and the canola R-line combination (Variety C5/Variety C6) with (Variety C7/Variety C8). In the former case, $M_T$ values of 100, 250 and 450 were considered (FIG. 5), in the latter case only $M_T$=200 (FIG. 6). Resampling of the markers was done at random for each of the 250 2W pools. The results are shown in FIG. 5 and FIG. 6 for the maize breeding cross combination and canola breeding cross combination, respectively. As shown in FIGS. 5 and 6, the DER increased with increasing p when the value of p was deliberately increased for the maize and canola breeding cross combinations. This decrease was observed regardless of $M_T$, the target number of polymorphic markers per breeding cross. However, the absolute level of the DER was lower for higher values of $M_T$. In the maize example, the DER at p=50% was around 5%, 1% and 0.5% for MT values of 100, 250, and 450, respectively (FIG. 5).

To summarize, the DER decreases with increasing number of markers ($M_G$) and increases with increasing proportion of markers polymorphic in both breeding crosses (p).

What DER level is deemed acceptable will depend on the intended usage of the marker genotypes. It is conceivable, for example, that applications that make use of all markers simultaneously, such as whole genome prediction or germplasm characterization, can tolerate a higher DER than applications that put more weight on individual markers, such as QTL mapping and marker assisted selection. The DER at a given level of p is the lower the more markers are genotyped ($M_G$). Put differently, the higher the desired number of informative markers per cross ($M_T$), the higher the p values that can be used. Finding the optimal p for a given breeding cross combination will require prediction of the DER or at least identifying an upper bound. This could be achieved by using information about the genetic distance between breeding crosses and the distribution of polymorphic markers. It is hypothesized that the DER will be lower the greater the genetic distance and the more even the distribution of markers within polymorphic regions. A prediction of the DER could also be obtained from a stochastic simulation, conducted in a similar way as in this study. This would give accurate predictions to the extent that the assumptions underlying the simulation are valid. The ability to predict the DER would also allow to optimize the choice of breeding crosses to combine in a pool and which markers to genotype.

Example 2

Real Data Validation and Proof of Feasibility

This real data validation study was conducted to demonstrate the feasibility of pooled genotyping and in-silico deconvolution in practice. The study comprised 208 different maize 2W pools of two DH lines from ten breeding cross combinations (SSS with SSS, NSS with NSS and SSS with NSS). The pools were genotyped with between 125 and 171 SNP markers polymorphic in at least one of the two breeding crosses comprising the pool (see Table 2). DNA of the pooled sample was extracted directly from a sample of pooled plant seed tissue of the individual DHs. The SNP markers were genotyped using a standard fluorescence based assay, for example, as described in Holland et al., (1991) Proc. Natl. Acad. Sci. 88:7276-7280, the content of which is incorporated herein by reference in its entirety. The deconvolution with HMM was performed using the equations (II), (V), and (VII) provided above. For validation purposes, genotyping was performed on the pooled DH lines individually for the same markers, which enabled the calculation of DER by comparing the deconvolved genotype scores with the observed scores. This comparison was only conducted for markers with observed scores in both individual DH. Because this varied slightly from pool to pool, the data is presented in Table 2 as averages of number of markers and of proportion of doubly polymorphic markers.

The average observed DER for markers polymorphic in both breeding crosses of the pool ranged between 2.4 and 7.0 (Table 2). For example, in one particular pool between DH progeny from the breeding cross combination (Variety M10/Variety M9) paired with (Variety M26/Variety M19), 155 markers were genotyped. Of those, 99 markers were polymorphic in the Variety M10/Variety M9 breeding cross, 98 markers were polymorphic in the Variety M26/Variety M19 breeding cross, and 42 markers were polymorphic in both breeding crosses. In this particular example, the deconvolved marker scores for doubly polymorphic markers matched the observed scores of the two DH in 41 out of 42 cases, leading to a DER of doubly polymorphic markers of 2.38%.

In general, the DER numbers observed in the real data validation agreed with those observed in the simulation studies. The DER tended to increase with increasing proportion of doubly polymorphic markers and decreasing number of genotyped markers. These trends were in agreement with the results from the simulation studies as well. Therefore, in-silico deconvolution is accurate and feasible in practice.

Example 3

Pooling More than Two DH

Pooling and in-silico deconvolution is not limited to 2W pools. To demonstrate this, the present method was applied to simulated pools of three (3W) and four (4W) DH lines from different maize breeding crosses (Table 3). The 3W and 4W pools were simulated as previously described for the 2W pools. When all three/four pooled DH had the same allele, the pool received an observed marker score of 0 or 2, depending on the allele. If the pooled DH lines had different alleles, the pool received the heterozygous score of 1. This implies a genotyping technology that can identify the presence of multiple alleles in the pool, but not necessarily their exact distribution (i.e., the number of copies of each allele). All markers polymorphic in at least one of the breeding crosses comprising the pool were used. This resulted in more than 1,500 available markers for most pools (Table 3). For each breeding cross combination 100 unique pools were generated. The in-silico deconvolution was conducted as previously described using transmission and emission matrices adapted to the 3W and 4W cases. The DER was determined by comparing the deconvolved scores with the true scores of the pooled DH lines, as before. This provided the ability to distinguish between markers polymorphic in one, two, three, and four of the breeding crosses of the pool. Reported in Table 3 are averages across the 100 pools for each breeding cross combination.

The DER was below 3% for the 3W pools and below 5.5% for the 4W pools (Table 3). The DER was higher the more breeding crosses a marker was polymorphic in. It should be noted that in contrast to 2W pools, deconvolution is not necessarily trivial and 100% exact for markers polymorphic in only one of the breeding crosses. This is because several grandparental arrangements can result in heterozygous pool genotypes, thereby preventing an unequivocal solution. The exception to this is when all breeding crosses

TABLE 2

Summary of results for real maize 2W pools of the validation and practical feasibility study

| Breeding cross combination | # Observations | $M_G$ | p (%) | DER (%) singly | DER (%) doubly |
|---|---|---|---|---|---|
| SSS with SSS | | | | | |
| (Variety M22/Variety M23) -- (Variety M4/Variety M22) | 16 | 125.3 | 48.5 | 4.8 | 7.0 |
| (Variety M22/Variety M23) -- (Variety M7/Variety M25) | 16 | 131.5 | 49.6 | 3.6 | 5.1 |
| (Variety M4/Variety M24) -- (Variety M7/Variety M25) | 24 | 154.5 | 49.5 | 4.8 | 6.9 |
| NSS with NSS | | | | | |
| (Variety M10/Variety M9) -- (Variety M26/Variety M19) | 24 | 153.5 | 26.7 | 2.0 | 3.9 |
| SSS with NSS | | | | | |
| (Variety M22/Variety M23) -- (Variety M10/Variety M9) | 16 | 125.3 | 28.2 | 2.5 | 4.6 |
| (Variety M22/Variety M23) -- (Variety M26/Variety M19) | 16 | 135.7 | 28.4 | 2.6 | 3.2 |
| (Variety M4/Variety M24) -- (Variety M10/Variety M9) | 24 | 161.7 | 25.7 | 1.3 | 2.6 |
| (Variety M4/Variety M24) -- (Variety M26/Variety M19) | 24 | 159.8 | 31.7 | 1.4 | 2.4 |
| (Variety M7/Variety M25) -- (Variety M10/Variety M9) | 24 | 168.6 | 24.5 | 2.0 | 3.5 |
| (Variety M7/Variety M25) -- (Variety M26/Variety M19) | 24 | 171.3 | 27.9 | 1.3 | 2.7 |

A pool comprised one DH from each of the named breeding crosses. Reported are averages over all observations for breeding cross combination. $M_G$ is number of genotyped markers and p is the proportion of markers polymorphic in both breeding crosses. Deconvolution Error Rate (DER) singly/doubly - % erroneous genotype scores of all markers polymorphic in one/both of the breeding crosses.

in which the marker is not segregating have the same allele. The DER for markers polymorphic in only one breeding cross was very low (<0.5%), however.

In conclusion, pooled genotyping with in-silico deconvolution can be applied to pools of more than two DH and delivers accurate results, at least for higher marker densities.

The forward pass is executed from k=1 to k=M and the backward pass from k=M to k=1. The posterior ancestral inheritance probabilities at locus k are then obtained by calculating:

$$p_k = (f_k \circ b_{k+1})([f_k \circ b_{k+1}]'1)^{-1} \quad (VII)$$

TABLE 3

Summary of results for simulated maize 3W and 4W pools.

| | # Markers polymorphic in | | | | DER (%) for markers polymorphic in | | | |
|---|---|---|---|---|---|---|---|---|
| Breeding cross combination | one | two | three | four | one | two | three | four |
| (Variety M27/Variety M28)--(Variety M16/Variety M29)--(Variety M3/Variety M30) | 1040 | 692 | 117 | — | 0.3 | 1.6 | 2.4 | — |
| (Variety M31/Variety M8)--(Variety M32/Variety M33)--(Variety M34/Variety M35) | 950 | 498 | 87 | — | 0.3 | 2.3 | 2.3 | — |
| (Variety M36/Variety M37)--(Variety M24/Variety M7)--(Variety M34/Variety M15) | 1155 | 576 | 49 | — | 0.3 | 0.9 | 1.3 | — |
| (Variety M38/Variety M39)--(Variety M34/Variety M40)--(Variety M41/Variety M42) | 1127 | 257 | 20 | — | 0.3 | 1.2 | 1.5 | — |
| (Variety M16/Variety M20)--(Variety M43/Variety M44)--(Variety M45/Variety M46)--(Variety M5/Variety M47) | 805 | 739 | 517 | 153 | 0.2 | 1.7 | 3.2 | 4.4 |
| (Variety M48/Variety M49)--(Variety M41/Variety M13)--(Variety M15/Variety M50)--(Variety M34/Variety M51) | 706 | 487 | 169 | 25 | 0.5 | 2.7 | 5.6 | 5.1 |
| (Variety M38/Variety M29)--(Variety M2/Variety M52)--(Variety M53/Variety M48)--(Variety M31/Variety M41) | 1230 | 656 | 160 | 30 | 0.5 | 1.5 | 2.8 | 4.4 |

A pool comprised one DH from each of the named breeding crosses. Reported are averages over all 100 observations per breeding cross combination.
DER (Deconvolution Error Rate in %) is the percent of erroneous genotype scores among markers polymorphic in one/two/three/four of the breeding crosses.

Example 4

Application to Sequencing Data

The HMI for sequence read data can be implemented with the forward-backward algorithm as described in Rabiner (1989) Proc. IEEE 77:257-286, the content of which is incorporated herein by reference in its entirety. Given a locus k, with an emission matrix $E_k$, a transition matrix $T_k$, and a vector of forward probabilities from the previous calculation (henceforth denoted as $f_{k-1}$), the forward pass is:

$$f_k = (T'_k f_{k-1}) \circ E_{k[m,]} \quad (I)$$

where [m,] specifies the row of the emission matrix for the observed genotype m (e.g., m counts of a reference allele), "∘" refers to element-wise multiplication. In some embodiments, equation (I) is modified to include a normalization constant $c_k$. Thus, equation (I) then becomes:

$$f_k = c_k^{-1}(T'_k f_{k-1}) \circ E_{k[m,]} \quad (II)$$

Where the normalization constant $c_k$ is equal to:

$$c_k = ((T'_k f_{k-1}) \circ E_{k[m,]})'1 \quad (III)$$

In some embodiments, the backward algorithm then is:

$$b_k = T'_k(b_{k+1} \circ E_{k[m,]}) \quad (IV)$$

where $b_k$ indicates the vector of backward probabilities. In some embodiments, equation (IV) is modified to include a normalization constant $\alpha_k$. Thus, equation (IV) then becomes:

$$b_k = \alpha_k^{-1} T'_k(b_{k+1} \circ E_{k[m,]}) \quad (V)$$

and $\alpha_k$ is similarly defined as $c_k$ where:

$$\alpha_k = (T'_k(b_{k+1} \circ E_{k[m,]}))'1 \quad (VI)$$

The initial vector of forward probabilities $f_0$, which is used when k=1, corresponds to the prior probabilities for the crosses involved in the pool. For instance, for a 2W pool of $F_1$ derived DH/H lines $f_0 = [0.25\ 0.25\ 0.25\ 0.25]'$ (i.e., the products of the expected parental genome contributions to the crosses, which are all equal to 0.5 in the case of $F_1$ crosses), the initial $b_{M+1}$, where M is the number of markers, for the backward pass is always [1 1 1 1]' (i.e., a vector of appropriate dimensions filled with 1's).

Depicted in FIG. 7 is a non-limiting exemplary embodiment of the present methods. Shown in FIG. 7 are parent plants, $I_1$, $I_2$, $I_3$, and $I_4$, which were crossed in two parental crosses $I_1/I_2$ and $I_3/I_4$. In this embodiment, the genotypes of the parent plants (i.e., ancestors) at the marker loci designated $L_1$, $L_2$, and $L_3$ are known. The allele calls for each parent and the pedigree relationships between the parent plants and progeny plants $P_1$ and $P_2$ are depicted. As shown in FIG. 7, progeny plants $P_1$ and $P_2$ are the offspring of parental crosses $I_1/I_2$ and $I_3/I_4$, respectively. While FIG. 7 reveals that progeny $P_1$ received marker alleles from parent plant $I_2$ at all three loci and progeny $P_2$ has received the marker allele at $L_1$ from parent plant $I_4$ and the marker alleles at loci $L_2$ and $L_3$ from parent plant $I_3$, it should be understood that this information is not known prior to the in-silico deconvolution step. In this embodiment, the progeny plants are not genotyped individually, but rather genomic DNA is isolated from each of the progeny plants and pooled to produce a pooled progeny genomic DNA. Alternatively, the pooled DNA sample is extracted from a pooled tissue sample. The pooled progeny DNA is then genotyped using any suitable genotyping technique. The forward-backward HMM can then be implemented to deconvolve the genotypes of $P_1$ and $P_2$ at marker loci $L_1$, $L_2$, and $L_3$.

The transition matrix $T_k$ for locus k describes the conditional probabilities that the pattern of inheritance at locus k–1 will result in a particular inheritance pattern at locus k. For example, it describes the probability that the pooled individuals inherited from ancestors $I_1$ and $I_3$ at locus $L_2$, conditional on them inheriting from $I_2$ and $I_3$ at locus $L_1$. In general, $T_k$ for a 2W pool is (labels not part of computation):

$$T_k = \begin{array}{c} I_1 - I_3 \\ I_1 - I_4 \\ I_2 - I_3 \\ I_2 - I_4 \end{array} \begin{bmatrix} (1-r_k)^2 & r_k(1-r_k) & r_k(1-r_k) & r_k^2 \\ r_k(1-r_k) & (1-r_k)^2 & r_k^2 & r_k(1-r_k) \\ r_k(1-r_k) & r_k^2 & (1-r_k)^2 & r_k(1-r_k) \\ r_k^2 & r_k(1-r_k) & r_k(1-r_k) & (1-r_k)^2 \end{bmatrix}$$

where $r_k$ is the recombination frequency between loci k and k-1. The recombination frequency can be calculated with the mapping function of Haldane (see Haldane (1919) J. Genet. 8:299-309, the content of which is incorporated herein by reference in its entirety) from the genetic map distance between two marker loci ($d_k$, in Morgans) as:

$$r_k = \frac{1 - e^{-2d_k}}{2} \quad \text{(VIII)}$$

In the exemplary embodiments shown in FIG. 7, the distance between locus $L_2$ and $L_1$ is 0.10 and that $L_3$ and $L_2$ is 0.05, which translates to $r_2$=0.091 and $r_3$=0.048. Because locus $L_1$ is located at the start of the chromosome and is hence not linked to any previous locus, $r_1$=0.500. Other mapping functions could have been used (e.g., Kosambi, (1943) Ann. Eugen. 12: 172-175, the content of which is incorporated herein by reference in its entirety). Substituting these values for $r_k$ gives the following transition matrices for the three loci (small discrepancies are possible due to rounding error).

$$T_1 = \begin{array}{c} I_1 - I_3 \\ I_1 - I_4 \\ I_2 - I_3 \\ I_2 - I_4 \end{array} \begin{bmatrix} 0.250 & 0.250 & 0.250 & 0.250 \\ 0.250 & 0.250 & 0.250 & 0.250 \\ 0.250 & 0.250 & 0.250 & 0.250 \\ 0.250 & 0.250 & 0.250 & 0.250 \end{bmatrix}$$

$$T_2 = \begin{array}{c} I_1 - I_3 \\ I_1 - I_4 \\ I_2 - I_3 \\ I_2 - I_4 \end{array} \begin{bmatrix} 0.827 & 0.082 & 0.082 & 0.008 \\ 0.082 & 0.827 & 0.008 & 0.082 \\ 0.082 & 0.008 & 0.827 & 0.082 \\ 0.008 & 0.082 & 0.082 & 0.827 \end{bmatrix}$$

$$T_3 = \begin{array}{c} I_1 - I_3 \\ I_1 - I_4 \\ I_2 - I_3 \\ I_2 - I_4 \end{array} \begin{bmatrix} 0.907 & 0.045 & 0.045 & 0.002 \\ 0.045 & 0.907 & 0.002 & 0.045 \\ 0.045 & 0.002 & 0.907 & 0.045 \\ 0.002 & 0.045 & 0.045 & 0.907 \end{bmatrix}$$

The emission matrix $E_k$ for locus k describes the probabilities of an observed marker genotype conditional on the ancestral inheritance pattern of the pool. The count data generated by sequencing platforms can be modeled using a beta-binomial probability distribution. Briefly, the beta-binomial distribution models the probability of observing m reads of a reference allele out of n total sequence reads, when the underlying allele frequency in the sample is uncertain. An arbitrary allele of the locus can be chosen as reference allele. Specifically, the probability of observing m reference allele reads out of n total reads is $$P(m \mid n, \alpha, \beta) = \binom{n}{m} \frac{B(m + \alpha, n - m + \beta)}{B(\alpha, \beta)} \quad \text{(IX)}$$

where B is the Beta function and $\alpha$ and $\beta$ are positive parameters that reflect the underlying uncertainty in the reference allele frequency. In general, when $\alpha > \beta$, the frequency of the allele will tend to be >0.5, when $\beta > \alpha$, it will tend to be <0.5 and when $\alpha = \beta$ it will be equal to 0.5, on average. Further, the smaller $\alpha + \beta$, the higher the degree of uncertainty in the frequency. When this sum becomes very large, the beta-binomial model approximates the binomial model. We calculated both parameters as follows $$\alpha = \begin{cases} v, & \text{if } \pi < 0.5 \\ -\frac{\pi v}{\pi - 1}, & \text{else} \end{cases} \quad \text{(X)}$$

$$\beta = \begin{cases} -(\pi - 1)v/\pi, & \text{if } \pi < 0.5 \\ v, & \text{else} \end{cases} \quad \text{(XI)}$$

where $\pi$ is a prior estimate of the reference allele frequency and $v$ a dispersion parameter that governs the amount of uncertainty around it (the smaller $v$, the greater the uncertainty, with $v > 0$). Estimates of $\pi$ can be obtained by first estimating the read proportion of each of the pooled pedigrees in the sample and then summing over those pedigrees that contribute the reference allele in a given parental configuration. The pedigree proportions can be estimated for example from the read data of marker loci that are monomorphic within each pedigree but for alternate alleles. In the absence of prior estimates, they should be assumed to be equal. For parental configurations in which all or none of the pedigrees contribute the reference allele, $\pi$ might be set to 0.99 and 0.01 (or similar values), respectively, to allow for the possibility of genotyping error and avoid division by zero. In the case of missing data, i.e., n=0, the emission matrix reduces to a row vector of 1's.

To continue the example in FIG. 7, for loci $L_1$, $L_2$ and $L_3$, respectively, the following reference allele and total allele counts were observed: $m_1$=0, $n_1$=3; $m_2$=3, $n_2$=8; $m_3$=2, $n_3$=6 (the reference allele being that of parent $I_1$). The pedigree proportions are estimated to be 0.6:0.4 for $I_1/I_2$ and $v$ is set to 2.5. The emission matrices for the three loci are then (labels not part of computation):

$$E_1 = \begin{array}{c} \\ m=0 \\ m=1 \\ m=2 \\ m=3 \end{array} \begin{bmatrix} I_1-I_3 & I_1-I_4 & I_2-I_3 & I_2-I_4 \\ 0.00 & 0.11 & 0.00 & 0.11 \\ 0.00 & 0.26 & 0.00 & 0.26 \\ 0.03 & 0.36 & 0.03 & 0.36 \\ 0.07 & 0.27 & 0.97 & 0.27 \end{bmatrix}$$

$$E_2 = \begin{array}{c} \\ m=0 \\ m=1 \\ m=2 \\ m=3 \\ m=4 \\ m=5 \\ m=6 \\ m=7 \\ m=8 \end{array} \begin{bmatrix} I_1-I_3 & I_1-I_4 & I_2-I_3 & I_2-I_4 \\ 0.00 & 0.01 & 0.08 & 0.92 \\ 0.00 & 0.04 & 0.14 & 0.97 \\ 0.00 & 0.08 & 0.18 & 0.00 \\ 0.00 & 0.12 & 0.18 & 0.00 \\ 0.00 & 0.16 & 0.16 & 0.00 \\ 0.00 & 0.18 & 0.12 & 0.00 \\ 0.00 & 0.18 & 0.08 & 0.00 \\ 0.07 & 0.14 & 0.04 & 0.00 \\ 0.92 & 0.08 & 0.01 & 0.00 \end{bmatrix}$$

$$E_3 = \begin{array}{c} \\ m=0 \\ m=1 \\ m=2 \\ m=3 \\ m=4 \\ m=5 \\ m=6 \end{array} \begin{bmatrix} I_1-I_3 & I_1-I_4 & I_2-I_3 & I_2-I_4 \\ 0.00 & 0.00 & 0.12 & 0.12 \\ 0.00 & 0.00 & 0.20 & 0.20 \\ 0.00 & 0.00 & 0.23 & 0.23 \\ 0.00 & 0.00 & 0.20 & 0.20 \\ 0.00 & 0.00 & 0.15 & 0.15 \\ 0.06 & 0.06 & 0.08 & 0.08 \\ 0.94 & 0.94 & 0.03 & 0.03 \end{bmatrix}$$

For example, to compute the emission probability of m=3 for configuration $I_2$-$I_3$ at locus $L_2$, one first determines $\pi$, which is 0.4, because the reference allele is contributed by the parent from the second pedigree, which has a pool proportion of 0.4. Then one computes a and according to equations (X) and (XI), which turn out to be α=2.5 and β=3.75. Entering those numbers together with the values for v, n and m, which are 2.5, 8 and 3, respectively, into (IX) results in 0.18.

With the transition and emission matrices in place, the forward and backward probabilities $f_k$ and $b_k$ are then calculated. Starting at k=1, the forward probabilities according to equation (II) are:

$$f_1 = c_1^{-1}(T_1'f_0) \circ E_{1[\theta_1]}$$
$$= (0.000 \quad 0.500 \quad 0.000 \quad 0.500)'$$

$$f_2 = c_2^{-1}(T_2'f_1) \circ E_{2[3,]}$$
$$= (0.000 \quad 0.872 \quad 0.127 \quad 0.001)'$$

$$f_3 = c_3^{-1}(T_3'f_2) \circ E_{3[2,]}$$
$$= (0.000 \quad 0.000 \quad 0.718 \quad 0.282)'$$

and starting from k=3, the backward probabilities according to equation (V) are:

$$b_3 = a_3^{-1}T_3'(b_4 \circ E_{3[2,]})$$
$$= (0.024 \quad 0.024 \quad 0.476 \quad 0.476)'$$

$$b_2 = a_2^{-1}T_2'(b_3 \circ E_{2[3,]})$$
$$= (0.082 \quad 0.035 \quad 0.799 \quad 0.083)'$$

$$b_1 = a_1^{-1}T_1'(b_2 \circ E_{1[\theta_1]})$$
$$= (0.250 \quad 0.250 \quad 0.250 \quad 0.250)'$$

Finally, after applying equation (VII) and arranging the results in a matrix the posterior ancestral inheritance probabilities $p_k$ are obtained (see Figure 7) as follows:

$$p_k = \begin{array}{c} \\ L_1 \\ L_2 \\ L_3 \end{array} \begin{bmatrix} I_1-I_3 & I_1-I_4 & I_2-I_3 & I_2-I_4 \\ 0.000 & 0.298 & 0.000 & 0.702 \\ 0.000 & 0.254 & 0.741 & 0.005 \\ 0.000 & 0.000 & 0.718 & 0.282 \end{bmatrix}$$

So, for example, the posterior probability that the pooled DH individuals inherited from $I_2$ and $I_3$ at locus $L_2$ is ≈¾ and that they inherited from $I_1$ and $I_4$ is ≈¼. Inheritance from $I_1$ and $I_3$ or $I_2$ and $I_4$ has very low probability because observing reads of alternate alleles (3 reference allele counts, 5 non-reference allele counts, in this example) is impossible when both ancestors carry the same allele. However, because the emission matrix allows for some genotyping errors, those probabilities are still positive. The pedigree information that progeny $P_1$ inherited from either $I_1$ or $I_2$ and progeny $P_2$ from either $I_3$ or $I_4$ is known. The most probable identity by decent (IBD) inheritance pattern is therefore that progeny $P_1$ inherited the chromosome segment between loci $L_1$ and $L_3$ entirely from $I_2$, whereas $P_2$ inherited a recombined chromosome segment, with the recombination from $I_4$ to $I_3$ happening between the loci $L_2$ and $L_3$. Based on this we can assign the most probable marker genotypes of the progeny. For progeny $P_1$ at locus $L_2$, for example, this is T and for $P_2$ at the same locus C.

For validation purposes and to assess the accuracy of the deconvolution process, the inferred marker genotypes obtained from the present methods can be compared with the observed marker scores of the pooled progeny plants. However, for many applications, such as whole genome prediction (see, e.g., Meuwissen et al., (2001) Genetics 157:1819-1829, the content of which is incorporated herein by reference in its entirety), the ancestral inheritance probabilities $p_k$ could be used directly.

Real Data Validation

The study comprised 8 DH from one heterotic group (GROUP1) and 8 DH from an opposite heterotic group (GROUP2) that were combined into sixteen different 2W pools, eight 3W pools, and four 4W pools. The DHs from the GROUP1 were derived in equal numbers from the pedigrees (VARIETY1/VARIETY2) and (VARIETY3/VARIETY4), the GROUP2 DHs from the pedigrees (VARIETY5/VARIETY6), (VARIETY7/VARIETY8). For the 2W pools each GROUP1 pedigree was combined with each GROUP2 pedigree, with four unique combinations of DHs in each case. The 3W pools were generated by combining the two GROUP1 pedigrees with either of the GROUP2 pedigrees. The 4W pools were generated by combining one DH from each of the four GROUP1 and GROUP2 pedigrees. One of the 3W pool samples was discarded because of low data quality.

DNA was extracted from plant leaf tissue of each DH. Equal quantities of DNA from two, three or four DHs of different pedigrees were combined to form pooled DNA samples. The polynucleotides of the DNA pools were sequenced as was the DNA of single DH controls. For the purposes of this example we examined sequence reads covering 2520 SNPs with known positions on the genetic map, which served as markers across all 10 maize chromosomes. Within a sample, each marker was represented by zero or more sequence reads. The counts of reads with reference and alternate alleles at a SNP marker were used as data for deconvolution. SNPs with zero reads in a sample were removed from the analysis as they provide no information for deconvolution. At SNPs that are polymorphic within a pool, the relative abundance of reference and alternate alleles varies due to sampling error which is accounted for by the beta-binomial model.

Deconvolution for markers that are monomorphic in all breeding crosses comprising the pool does not require the HMM algorithm, but instead was done by assigning the allele of the corresponding set of parents. This was done in a post-processing step. As described above, markers monomorphic for alternate alleles were, however, used to estimate the pedigree proportions in each pool and from that π.

For markers with one or more sequence reads, that were polymorphic in at least one of the breeding crosses in the pool, the deconvolution with the HMM was performed using the algorithm provided above.

For validation purposes, the DH involved in the pools were also genotyped individually in two replications. These controls allowed assessment of deconvolution accuracy by comparing the deconvolved marker scores with those from the control. Specifically, the deconvolution error rate was calculated as the percent of markers for which the HMM genotype of a DH did not match the control. For this only markers were used that fulfilled all of the following quality criteria: (1) one or more sequence reads in the pooled sample, (2) control had no parent-progeny inconsistencies, (3) no heterozygous calls in control and (4) identical genotypes in both replications of the control.

The average observed DER for markers polymorphic in at least one breeding cross of the pool ranged between 0.24% for 2W pools and 1.45 for 4W pools (Table 4). For example, in one particular 2W pool between DH progeny from the breeding cross combination VARIETY1/VARIETY2 paired with VARIETY5/VARIETY6, 967 markers were polymorphic in at least one of the crosses and fulfilled all the criteria of validation markers outlined above. In this particular example, the deconvolved marker scores for polymorphic markers matched the observed scores of the DH from the first cross in 964 out of 967 cases and for the DH from the second cross in 967 out of 967 cases. This leads to a DER for the first DH of 0.31% and of 0.00% for the second DH.

TABLE 4

Summary of results for real maize 2W pools feasibility study. Reported are averages over all observations within one category (2W, 3W, 4W). Deconvolution Error Rate (DER) - % erroneous genotype scores of all validation markers polymorphic in at least one of the breeding crosses.

|  | # Observations | # polymorphic markers | # validation markers | DER |
| --- | --- | --- | --- | --- |
| 2W | 16 | 1007 | 917 | 0.24% |
| 3W | 7 | 1272 | 1110 | 0.94% |
| 4W | 4 | 1417 | 1218 | 1.45% |

Example 5

Application of the Sequencing Method to Multiple Species

This example demonstrates genotyping of pooled samples of multiple species. One or more individuals of two or more different species can be combined in the same pool (a multi-species pool). As demonstrated in this example, if genome sequences of the species to be genotyped are known and distinct from one another, then sequence reads can be assigned specifically to each species. The genotypes of lines of the same species can then each be deconvolved using the HMM method of Example 4. To demonstrate this, the sequence-based method of Example 4 was applied to multi-species pools of three DH lines (3W) where two of the DH lines are from different maize breeding crosses, and the third DH line was from a canola breeding cross.

The study comprised 6 maize DH from one heterotic group (GROUP1), 6 DH from an opposite heterotic group (GROUP2), and 6 canola DH. These DH were combined into 6 3W pools. Each pool consisted of one maize GROUP1 DH, one maize GROUP2 DH, and one canola DH. The maize DH from the GROUP1 were derived in equal numbers from the pedigrees (VARIETY1/VARIETY2) and (VARIETY3/VARIETY4), the GROUP2 DH from the pedigrees (VARIETY5/VARIETY6), (VARIETY7/VARIETY8). The canola DH were derived in equal numbers from pedigrees (VARIETY9/VARIETY10) and (VARIETY11/VARIETY12).

DNA was extracted from plant leaf tissue of each DH. Equal quantities of DNA from each DH were combined to form pooled DNA samples. For validation purposes, samples of single maize and canola DH and 2W pools of the maize DH alone served as controls. The polynucleotides of the DNA pools were sequenced as was the DNA of single DH and maize-only 2W controls. For the purposes of this example 2,278 SNPs canola-specific SNPs were examined, as were 2,869 SNPs maize-specific SNPs with genetic map positions. Genetic map positions are used in in-silico deconvolution of multiple DH from the same species, but are not necessary for the single Canola DH in this particular example. Sequence reads covering these polymorphisms served as markers across all 10 maize chromosomes and all 19 canola chromosomes. Within a sample, each marker was represented by zero or more sequence reads. Since there was only one canola DH per pool, the genotype of the canola DH could be determined directly from the genotype of the sequence reads covering each canola SNP marker, and no in silico deconvolution was necessary. For the maize DH, in silico deconvolution was performed as in Example 4 using the sequence reads covering the maize SNP markers. At SNPs that are polymorphic within a pool, the relative abundance of reference and alternate alleles varies due to sampling error which is accounted for by the beta-binomial model.

Deconvolution for markers that are monomorphic in all breeding crosses comprising the pool does not require the HMM algorithm, but instead was done by assigning the allele of the corresponding set of parents. This was done in a post-processing step. As in example 4, markers monomorphic for alternate alleles were, however, used to estimate the pedigree proportions in each pool and from that $\pi$. For markers with one or more sequence reads, that were polymorphic in at least one of the breeding crosses in the pool, the deconvolution with the HMM was performed using the algorithm provided in Example 4.

Each single DH was evaluated in one sample, whereas each 2W and 3W pool was evaluated in two technical replicates. To validate the ability of the pooled approach to correctly assign genotypes to the canola DH lines, the canola DH genotypes from the single DH controls and the 3W pools were compared to the previously known genotype of each canola DH obtained from an independent sequencing experiment. The genotyping error rate for the single DH averaged 0.174%, and the 3W pools averaged 0.198% (Table 5). For the maize DH, the deconvolution error rate (errors at markers polymorphic in at least one cross) for the maize 2W controls was 0.47% and that of the 3W pools with one canola DH was 0.45%, indicating that the maize DH could be effectively deconvolved in the presence of a canola DH. The multi-species method of pooled genotyping could also be applied to genetic marker technologies other than sequencing, provided the genetic markers are specific to each species.

TABLE 5

Summary of results for multiple-species 3W pools. Reported are averages over all observations within one category (single DH canola, 3W canola, 2W maize, 3W maize). Deconvolution Error Rate (DER) - % erroneous genotype scores of all validation markers polymorphic in at least one of the breeding crosses. Genotyping Error Rate (GER) - % erroneous genotype scores of all validation markers compared to a previously known genotype.

|  | # Observations | GER | DER |
| --- | --- | --- | --- |
| Single DH Canola | 6 | 0.17% | — |
| 3W Canola | 12 | 0.2% | — |
| 2W maize | 12 | — | 0.47% |
| 3W maize | 12 | — | 0.45% |

That which is claimed:

1. A method for selecting a DNA sample with increased genotyping efficiency by using multiple crop DNA pooling and deconvolution, the method comprising:

a. providing a pooled DNA sample comprising:
  i. a pooled genomic DNA sample comprising a genomic DNA sample isolated from a progeny plant of a first crop species, wherein the parental genotypes of said progeny plant of the first crop species are either previously known or simultaneously determined; and
  ii. a pooled genomic DNA sample comprising a genomic DNA sample isolated from a progeny plant of a second crop species, wherein the parental genotypes of said progeny plant of the second crop species are either previously known or simultaneously determined;
b. detecting in the pooled DNA sample at least one allele of a marker locus from the progeny plant of the first crop species and the progeny plant of the second crop species; and
c. analyzing the genotype of the pooled DNA sample for at least one marker locus detected in step (b), wherein analyzing the genotype comprises:
  i. building a first matrix $T_k$ for each marker locus detected in step (b) by calculating the probabilities that a pattern of inheritance at a previous marker locus can result in a pattern of inheritance at the marker locus based on the pedigree information and genetic map distance information;
  ii. building a second matrix $E_k$ for each marker locus detected in step (b) by calculating the probabilities that an observed genotype of the pooled genomic DNA sample could be produced by each permutation of inheritance from each parent plant in the parental cross that produced the progeny plant based on each detected allele in step (b) and the pedigree information;
  iii. determining a most probable genotype for the at least one marker locus detected in step (b) for each progeny plant, and
d. selecting the DNA sample based on the most probable genotype.

2. The method of claim 1, wherein the determining in step (c)(iii) comprises hidden Markov Modeling comprising calculating a vector of forward probabilities at the marker locus, calculating a backward vector of probabilities at the marker locus, and calculating posterior ancestral inheritance probabilities at the marker locus.

3. The method of claim 1, wherein the determining in step (d)(iii) comprises hidden markov modeling comprising: (A) calculating a vector of forward probabilities at the marker locus; (B) calculating a vector of backward probabilities at the marker locus; and (C) calculating posterior ancestral inheritance probabilities at the marker locus; wherein the calculating a vector of forward probabilities, calculating a vector of backward probabilities, and calculating posterior ancestral inheritance probabilities are expressed on a scale of natural logarithm (base e).

4. The method of claim 1, wherein step (a) further comprises at least three different parental breeding crosses for each crop species.

5. The method of claim 1, wherein step (a) further comprises at least four different parental breeding crosses for each crop species.

6. The method of claim 1, wherein step (b) further comprises at least 4, 5, 6, 7, 8, 9, 10, 11, 12, 13, 14, 15, 16, 17, 18, 19, or 20 alleles of each crop species.

7. The method of claim 1, wherein steps (b) and (c) utilize at least 100, 1,000, or 10,000 marker loci.

8. The method of claim 1, wherein at least one of the progeny plants of each species is a haploid, doubled haploid or a progeny plant derived without several generations of self-pollinations.

9. The method of claim 1, wherein the first and second crop species are maize or canola.

10. The method of claim 1, wherein at least one marker locus detected in step (b) is associated with one or more phenotypes.

11. The method of claim 10, wherein the one or more phenotypes are selected from the group consisting of yield, leaf angle, anthesis-silking interval, staygreen duration, early growth rate, overall growth rate, growth pattern, maximum biomass, total biomass, nitrogen use efficiency, water use efficiency, tocol content, oleic acid content, phytic acid content, amino acid composition, oil quantity or quality, energy availability, digestibility, fatty acid composition, a pathogen defense mechanism, lysine and sulfur levels, starch synthesis, disease, herbicide resistance, male sterility, plant vigor, nutrient content, hemicellulose content, cellulose production, cold tolerance, salt tolerance, heat tolerance, drought tolerance, grain moisture content, stalk lodging, root lodging, root pulling resistance, stand establishment, emergence, midsilk, test weight, protein content, starch percentage, relative maturity, plant height, seed size, heading date, resistance to insects, disease resistance, brittle snap, stalk breakage, resistance to fungus, seed moisture, head shape, hullability, seedling vigor, beginning to bloom date, maturity date, seed shatter, winter survival, fiber strength, ear height, plant barrenness, seed number, seed weight, and color grade.

12. A method for selecting a progeny plant with increased genotyping efficiency by using multiple crop DNA pooling and deconvolution, the method comprising:
  providing a pooled DNA sample comprising:
    a pooled genomic DNA sample comprising a genomic DNA sample isolated from at least one progeny plant a first crop species, wherein the parental genotypes of said at least one progeny plant of the first crop species are either previously known or simultaneously determined; and
    a pooled genomic DNA sample comprising a genomic DNA sample isolated from at least one progeny plant of a second crop species, wherein the parental genotypes of said at least one progeny plant of the second crop species are either previously known or simultaneously determined;
  detecting at least one allele of a marker locus from each progeny plant of each of the first crop species and the second crop species;
  comparing said alleles with expected alleles based on pedigree information and genetic map distance information;
  determining a most probable genotype for each progeny of each species, based on the comparison of the observed alleles with the expected alleles based on pedigree information and genetic map distance information, and
    selecting the progeny plant based on the most probable genotype.

13. The method of claim 12, wherein the comparison of the observed alleles and the expected alleles based on pedigree information and genetic map distance information is calculated by probabilistic deconvolution.

14. The method of claim 13, wherein the probabilistic deconvolution is hidden markov modeling or computational haplotype phasing.

15. The method of claim 12, wherein the comparison of the observed alleles and the expected alleles based on pedigree information and genetic map distance information is calculated by hidden markov modeling expressed on the scale of the natural logarithm (base e).

\* \* \* \* \*